US007919514B2

(12) United States Patent
Monenschein et al.

(10) Patent No.: US 7,919,514 B2
(45) Date of Patent: *Apr. 5, 2011

(54) THIADIAZOLE COMPOUNDS AND METHODS OF USE

(75) Inventors: Holger Monenschein, Camarillo, CA (US); James Thomas Rider, Woodland Hills, CA (US); Guomin Yao, Newbury Park, CA (US); Qingping Zeng, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 531 days.

This patent is subject to a terminal disclaimer.

(21) Appl. No.: 12/077,633

(22) Filed: Mar. 19, 2008

(65) Prior Publication Data

US 2008/0255145 A1  Oct. 16, 2008

Related U.S. Application Data

(63) Continuation of application No. 11/251,846, filed on Oct. 18, 2005, now Pat. No. 7,354,944.

(60) Provisional application No. 60/619,010, filed on Oct. 18, 2004.

(51) Int. Cl.
A61K 31/433 (2006.01)
C07D 285/12 (2006.01)

(52) U.S. Cl. ........ 514/363; 548/125; 548/136; 548/138; 514/361

(58) Field of Classification Search .................. 548/125, 548/136, 138; 514/361, 363
See application file for complete search history.

(56) References Cited

U.S. PATENT DOCUMENTS

| 3,452,035 A | 6/1969 | Berkelhammer et al. |
| 3,666,860 A | 5/1972 | Berkelhammer et al. |
| 3,740,434 A | 6/1973 | Berkelhammer et al. |
| 3,830,924 A | 8/1974 | Berkelhammer et al. |
| 3,842,174 A | 10/1974 | Berkelhammer et al. |
| 3,904,756 A | 9/1975 | Berkelhammer et al. |
| 3,991,200 A | 11/1976 | Berkelhammer et al. |
| 4,086,238 A | 4/1978 | Krenzer |
| 4,146,400 A | 3/1979 | Lowski et al. |
| 4,596,802 A | 6/1986 | Wermuth et al. |
| 5,086,053 A | 2/1992 | Brodin et al. |
| 5,834,401 A | 11/1998 | Kawamura et al. |
| 5,977,027 A | 11/1999 | Kawamura et al. |
| 6,323,315 B1 | 11/2001 | Pettit et al. |
| 6,420,400 B1 | 7/2002 | Zhang et al. |
| 6,620,911 B1 | 9/2003 | Pettit et al. |
| 6,894,054 B2 | 5/2005 | Laborde et al. |
| 7,354,944 B2 * | 4/2008 | Zeng et al. ............ 514/363 |
| 7,514,566 B2 * | 4/2009 | Zeng et al. ............ 548/198 |
| 2002/0115863 A1 | 8/2002 | Patel et al. |
| 2002/0119962 A1 | 8/2002 | Jacobs et al. |
| 2004/0102360 A1 | 5/2004 | Barnett et al. |
| 2004/0106540 A1 | 6/2004 | Barnett et al. |
| 2004/0122016 A1 | 6/2004 | Cao et al. |
| 2005/0043372 A1 | 2/2005 | Chen et al. |
| 2005/0053594 A1 | 3/2005 | Alessi et al. |
| 2005/0143384 A1 | 6/2005 | Sartori et al. |
| 2005/0148640 A1 | 7/2005 | Come et al. |
| 2005/0222219 A1 | 10/2005 | Chen et al. |
| 2006/0003944 A1 | 1/2006 | Glinka et al. |
| 2007/0173506 A1 | 7/2007 | Zeng et al. |
| 2008/0269243 A1 | 10/2008 | Monenschein et al. |

FOREIGN PATENT DOCUMENTS

| DE | 3407505 | 9/1985 |
| WO | WO 93/19054 | 9/1993 |
| WO | WO 96/38419 | 12/1996 |
| WO | WO 97/22360 | 6/1997 |
| WO | WO 99/31096 | 6/1999 |
| WO | WO 01/44178 | 6/2001 |
| WO | WO 01/44179 | 6/2001 |
| WO | WO 02/083064 | 10/2003 |
| WO | WO 03/084473 | 10/2003 |
| WO | WO 03/094831 | 11/2003 |
| WO | WO 2004/014864 | 2/2004 |
| WO | WO 2004/041813 A1 | 5/2004 |
| WO | WO 2004/046120 A2 | 6/2004 |
| WO | WO 2004/056789 | 7/2004 |
| WO | WO 2004/096131 | 11/2004 |
| WO | WO 2005/014554 | 2/2005 |
| WO | WO 2005/046678 | 5/2005 |
| WO | WO 2005/089443 | 9/2005 |
| WO | WO 2005/113762 | 12/2005 |
| WO | WO 2006/044860 A2 | 4/2006 |
| WO | WO 2006/045716 | 5/2006 |
| WO | WO 2007/084391 A2 | 7/2007 |
| WO | WO 2008/036308 A2 | 3/2008 |

OTHER PUBLICATIONS

Bellacosa, et al., "Molecular Alterations of the AKT2 Oncogene in Ovarian and Breast Carcinomas", *Int. J. Cancer*, 64, 280-285 (1995).
Besson, et al., "PTEN/MMAC/TEP1 in Signal Transduction and Tumorigenesis", *Eur. J. Biochem.*, 263, 605-611 (1999).
Blume-Jensen, et al., "Oncogenic Kinase Signalling", *Nature*, 411, 355-365 (2001).
Brodbeck, et al., "A Human Protein Kinase by with Regulatory Phosphorylation Sites in the Activation Loop and in the C-terminal Hydophobic Domain", *J. Biol. Chem.*, 274, 9133-9136 (1999).
Cheng, et al., "AKT2, a Putative Oncogene Encoding a Member of a Subfamily of Protein-Serine/Threonine Kinases, is Amplified in Human Ovarian Carcinomas", *Proc. Natl. Acad. Sci. U.S.A.*, 89, 9267-9271 (1992).
Cheng, et al.," Amplification of AKT2 in Human Pancreatic Cancer Cells and Inhibition of AKT2 Expression and Tumorigenicity by Antisense RNA", *Proc. Natl. Acad. Sci. U.S.A.*, 93, 3636-3641 (1996).
Czech, et al., "Signaling Mechanisms That Regulate Glucose Transport", *J. Biol. Chem.*, 274, 1865-1868 (1999).
Datta, et al. "Cellular Survival: A Play in Three AKTS", *Genes Dev.*, 13, 2905-2927 (1999).

(Continued)

*Primary Examiner* — Golam M Shameem
(74) *Attorney, Agent, or Firm* — Bernard P. Friedrichsen

(57) ABSTRACT

The invention relates to thiadiazole compounds useful for treating diseases mediated by protein kinase B (PKB). The invention also relates to the therapeutic use of such thiadiazole compounds and compositions thereof in treating disease states associated with abnormal cell growth, cancer, inflammation, and metabolic disorders.

9 Claims, No Drawings

OTHER PUBLICATIONS

Duan et al., "Phosphatidylinositol 3-Kinase Is Required for Insulin-Like Growth Factor-I-Induced Vascular Smooth Muscle Cell Proliferation and Migration", *Circ. Res.*, 86, 15-23 (2000).

Fennel, B. J. et al., "Effects of the Antimitotic Natural Product Dolastatin 10, and Related Peptides, on the Human Malarial Parasite Plasmodium Falciparum", *J. Antimicrobial Chemotherapy*, 51(4), 833-841 (2003).

Hackbarth Corinne K., et al., "N-Alkyl Urea Hydroxamic Acids as a New Class of Peptide Deformylase Inhibitors with Antibacterial Activity", *Antimicrobial Agents and Chemotherapy*, 46(9), 2752-2764 (2002).

Hemmings, Brian A., "AKT Signaling: Linking Membrance Events to Life and Death Decisions", *Science*, 275, 628-630 (1997).

Hill et al., "Identification of a Plasma Membrane Raft-Associated PKB Ser473 Kinase Activity that is Distinct from ILK and PDK1", *Current Biology*, 12, 1251-1255 (2002).

Hiremath, S.P. et al., "Synthesis of 2-Phenyl(indol-3-yl)isothiocyanates, 1-Substituted-3-(substituted-2'-phenylindol-3'yl)thiosemicarbazides and their Reactions", *Indian Journal of Heterocyclic Chemistry*, 2(2), 119-124 (1992).

Hiremath, S.P. et al., "Synthesis of Substituted Indolylthiadiazolines and Indolylisoxazolines", *Indian J. Chem.*, 30B(8), 744-748 (1991).

Hresko et al., "Phosphoinositide-Dependent Kinase-2 is a Distinct Protein Kinase Enriched in a Novel Cytoskeletal Fraction Associated with Adipocyte Plasma Membranes", *J. Biol. Chem.*, 278, 21615-21622 (2003).

Khwaja, "AKT is More Than Just a Bad Kinase", *Nature*, 401, 33-34 (1999).

Kidwai, Mazaahir et al, "Solid Supported Reaction of Substituted 2-Oxazoline with Amines Under Microwave Irradiation", *J. Chinese Chem. Soc.*, 50(5), 1075-1078 (2003).

Kidwai, Mazaahir, et al., "Microwave Induced Synthesis and Antibacterial Activity of Cephalosporin Derivatives Using Solid Support", *Bioorganic Chemistry*, 29(6), 380-386 (2001).

Kulik et al., "Antiapoptotic Signalling by the Insulin-Like Growth Factor I Receptor, Phosphatidylinositol 3-Kinase, and AKT", *Mol. Cell. Biol.*, 17, 1595-1606 (1997).

Kureishi, et al., "The HMG-CoA Reductase Inhibitor Simvastatin Acitivates the Protein Kinase AKT and Promotes Angiogenesis in Normocholesterolemic Animals", *Nat. Med.*, 6, 1004-1010 (2000).

Lawlor et al., "PKB/AKT: A Key Mediator of Cell Proliferation, Survival and Insulin Responses?", *J. Cell Sci.*, 114, 2903-2910 (2001).

Li, et al., "TEP1, Encoded by a Candidate Tumor Suppressor Locus, is a Novel Protein Tyrosine Phosphatase Regulated by Transforming Growth Facto $\beta^1$", *Cancer Res.*, 57, 2124-2129 (1997).

Lin, et al.,"AKT Suppresses Androgen-Induced Apoptosis by Phosphorylating and Inhibiting Androgen Receptor", *Proc. Natl. Acad. Sci. U. S. A.*, 98, 7200-7205 (2001).

Luo, et al., "Acute Modulation of Endothelial AKT/PKB Activity Alters Nitric Oxide-Dependent Vasomotor Acitivity In Vivo", *J. Clin. Invest.*, 106, 493-499 (2000).

Mazzone et al., "Synthesis and Local Anesthetic Activity of Alkylaminoacyl Derivatives of 2-Amino-1,3,4- Thiadiazole", *II Farmaco*, 48(9), 1207-1224 (1993).

Miao et al., "Intracoronary, Adenovirus-Mediated AKT Gene Transfer In Heart Limits Infarct Size Following Ischemia-Reperfusion Injury In Vivo", *J. Mol. Cell. Cardiol.*, 32, 2397-2402 (2000).

Namikawa, et al., "AKT/Protein Kinase B Prevents Injury-Induced Motoneuron Death and Accelerates Axonal Regeneration", *J Neurosci.*, 20, 2875-2886 (2000).

Nicholson, et al., "The Protein Kinase B/AKT Signalling Pathway In Human Malignancy", *Cell. Signal.*, 14, 381-395 (2002).

Pachhamia et al., "Studies on Thiadiazoles: Part-1: Preparation and Antimicrobial Activitiy of 2-(αCarbamylarylmethy-Lamino)-5-(4'-Pyridy1)-1, 3, 4-Thiadiazoles", *J. Inst. Chemists (India)*, 61, 54-56 (1989).

Pande, Kalpana, et al., "Anti-inflammatory and Antiproteolytic Activities of Substituted Imidazolones", *Indian Drugs*, 23(1), 13-17 (1985).

Pettit, Robin K., et al., "Specific Activities of Dolastatin 10 and Peptide Derivatives Against Cryptococcus Neoformans", *Antimicrobial Agents and Chemotherapy*, 42(11), 2961-2965 (1998).

Senapati, R.M., et al., "Thiadiazoles", *Proceedings of the Institution of Chemists (India)*, 37(3), 111-113 (1965).

Shah et al., Studies on Actamide Derivatives : "Preparation and Antimircrobial Activity of 2-α-Arylaminoacetamido/α-Carbamoyl Benzylamino/ Arylcarbamoylmethylamino-5-o-Nitrophenyl/ Benzoylaminomethyl-1,3,4-Thiadiazole", *J. Indian Chem. Soc.*, LIX, 678-680 (1982).

Singh et al., "Synthesis, Characterization and Fungitoxicity of Manganses (II), Iron (II), Cobalt (II), Nickel (II), Copper (II) and Zinc (II) Complexes of N-Phenyl-5-Phenyl-1,3,4-Oxadiazole-2-Sulphonamide and 5- Phenyl-1,3,4-Oxadiazole-2-Imino Sulphonamide", *Indian J. Chem.*, 33A, 350-353 (1994).

Suzuki, Norio et al., "Synthesis and Antiallergy Activity of [1,3,4]Thiadizolo[3,2-a]-1,2,3,-triazolo[4,5- d]pyrimidin-9(3H)-one", *Chem. Pharm. Bull.*, 40(2), 357-363 (1992).

Testa et al., "AKT Plays a Central Role in Tumorigenesis", *Proc. Natl. Acad. Sci.*, 98, 10983-10985 (2001).

Verdu, et al., "Cell-Autonomous Regulation of Cell and Organ Growth in Drosophila by AKT/PKB", *Nat. Cell Biol.*, 1, 500-506 (1999).

Vivanco, et al., "The Phosphatidylinositol 3-Kinase-AKT Pathway in Human Cancer", *Nat. Rev. Cancer*, 2, 489-501 (2002).

Yadav et al., "A Facile Ring Transformation of 5-Oxazolone Derivatives to New 1,3,4-Oxa(thia)diazolo[3,2-a]pyrimidin-5-ones", *Indian J. Chem.*, 34B, 500-503 (1995).

Yang et al., "AKT/Protein Kinase B Signaling Inhibitor-2, a Selective Small Molecule Inhibitor of AKT Signaling with Antitumor Activity in Cancer Cells Overexpressing AKT", *Cancer Res.*, 64, 4394-4399 (2004).

Yuan, et al., "Frequent Activation of AKT2 and Induction of Apoptosis by Inhibition of Phosphoinositide-3-OH Kinase/AKT Pathway in Human Ovarian Cancer", *Oncogene*, 19, 2324-2330 (2000).

Fathalla et al., "Synthesis of Some New 1,8-Naphthyridine Derivatives of Expected Biological Activity", *Egyptian J, Chem.*, 46(1), 135-152 (2003).

International Search Report for copending PCT/US2005/037374 (WO 2006/044860), published by World Intellectual Property Organization on Apr. 27, 2006.

Mishra L., et al., "Synthesis and Fungicidal Activity of Some 5-Membered Heterocyclic Derivatives Containing Benzimidazoles," Biosci. Biotech. and Biochem. 57(6), pp. 989-991 (1993).

Zhuravel, I. 0. et al., "Synthesis of Substituted 3-(5-Amino-[1,3,4]thiadiazol-2-yl)-2H-pyrano [2,3-c]pyridin-2-ones," J. Heterocyc. Chem. 41(4), pp. 517-524 (2004).

Hanada, Masahito, et al., "Structure, Regulation and Function of PKB/AKT-A Major Therapeutic Target," Biochim. et Biophys. Acta 1697, pp. 3-16 (2004).

Supplementary European Search Report for EP 05812533 dated Oct. 16, 2009.

\* cited by examiner

THIADIAZOLE COMPOUNDS AND METHODS OF USE

1. CROSS REFERENCES TO RELATED APPLICATIONS

This application is a continuation of and claims priority to, U.S. patent application Ser. No. 11/251,846, filed on Oct. 18, 2005, now U.S. Pat. No. 7,354,944, which claims priority to U.S. Provisional Application No. 60/619,010, filed on Oct. 18, 2004, the contents, both of which, are hereby incorporated by reference in their entireties and for all purposes as is specifically set forth herein.

2. FIELD OF THE INVENTION

The invention relates to thiadiazole compounds useful for treating diseases mediated by protein kinase B (PKB). The invention also relates to the therapeutic use of such thiadiazole compounds and compositions thereof in treating disease states associated with abnormal cell growth, cancer, inflammation, and metabolic disorders.

3. BACKGROUND OF THE INVENTION

Protein kinases represent a large family of proteins which play a central role in the regulation of a wide variety of cellular processes, maintaining control over cellular function. A partial list of such kinases includes ab1, AKT, bcr-ab1, Blk, Brk, Btk, c-kit, c-met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, GSK3α, GSK3β, Hck, IGF-1R, INS-R, Jak, KDR, Lck, Lyn, MEK, MK2, MSK1, p38, PDGFR, PIK, PKB, PKA, PRAK, PRK2, PKC, PYK2, P70S6, ROCK2, ros, tie, tie2, TRK, Yes, and Zap70. Inhibition of such kinases has become an important therapeutic target.

AKT (also known as protein kinase B (PKB) or Rac-PK-beta), and its gene family products, has been identified as a serine/threonine protein kinase. Testa et al., *Proc. Natl. Acad. Sci.*, 2001, 98, 10983-10985; Lawlor et al., *J. Cell Sci.*, 2001, 114, 2903-2910; Duan, *Circ. Res.*, 2000, 86, 15-23. Three isoforms of PKB are currently known, PKBα (AKT1), PKBβ (AKT2), and PKBγ (AKT3). Cheng, *Proc. Natl. Acad. Sci. USA*, 1992, 89, 9267-9271; Brodbeck, et al., *J. Biol. Chem.* 1999, 274, 9133-9136. PKB mediates many effects of IGF-1 and other growth factors on tumor growth and inhibition of apoptosis. Nicholson, et al., *Cell. Signal.*, 2002, 14, 381-395. PKB plays an important role in cell proliferation, apoptosis and response to insulin. For these reasons, modulation of PKBs is of interest in the treatment of tumorigenesis, abnormal cell proliferation, and diabetes.

The molecular structure of the PKBs comprises a regulatory site near the carboxy terminus of the polypeptide, a catalytic domain with an activation loop having a threonine, and an amino-terminal pleckstrin homology domain. The pleckstrin homology domain permits anchorage of the enzyme to the cell membrane through interaction with phospholipids, which triggers the activation of the PKBs. The role of pleckstrin homology domain requires phosphorylation of phosphatidylinositol at the D-3 position via phosphatidylinositol 3-kinase PI3K, an SH2 domain protein that associates with activated receptor tyrosine kinases, particularly IGF-IR. In particular, phosphoinositol-3-kinase, when activated by receptor tyrosine kinase, catalyzes the synthesis of phosphoinositol-3,4-diphosphate and phosphatidylinositol 3,4,5-triphosphate. The pleckstrin homology domain binds 3-phosphoinositides, which are synthesized by PI3K upon stimulation by growth factors such as platelet derived growth factor (PDGF), nerve growth factor (NGF) and insulin-like growth factor (IGF-1). Kulik et al., *Mol. Cell. Biol.*, 1997, 17, 1595-1606; Hemmings, *Science*, 1997, 275, 628-630; Datta, et al. *Genes Dev.*, 1999, 13, 2905-2927. Lipid binding to the pleckstrin homology domain promotes translocation of PKB to the plasma membrane. Further activation of PKB occurs by phosphorylation by another protein kinase, PDK1 at Thr308, Thr309, and Thr305 for the PKB isoforms 1, 2 and 3, respectively. A third step of activation is catalyzed by a kinase that phosphorylates Ser473, Ser474 or Ser472 in the C-terminal tails of PKB/AKT-1, -2 and -3 respectively. The Ser473 kinase activity has been identified to be associated with plasma membrane and is not due to PKB and PDK1 kinase activity. Hill et al., *Current Biology*, 2002, 12, 1251-1255; Hresko et al., *J. Biol. Chem.*, 2003, 278, 21615-21622. The process produces the fully activated form of PKB.

Activation of PKB can also occur by inhibiting the D-3 phosphoinositide specific phosphatase, PTEN, which is a membrane-associated FYVE finger phosphatase commonly inactivated in many cancers, including prostate cancer. Besson, et al., *Eur. J. Biochem.*, 1999, 263, 605-611; Li, et al., *Cancer Res.*, 1997, 57, 2124-2129.

The catalytic domain of PKB is responsible for the phosphorylation of serine or threonine in the target protein.

Once activated, PKB mediates several cellular functions including proliferation, cell growth, and promotion of survival. Intracoronary, adenovirus-mediated akt gene transfer in heart limits infarct size following ischemia-reperfusion injury in vivo. Miao et al., *J. Mol. Cell. Cardiol.*, 2000, 32, 2397-2402. The antiapoptotic function of PKB is reported to be mediated by its ability to phosphorylate apoptosis regulatory molecules including BAD, caspase 9, IKK-, and the forkhead transcriptional factor FKHRL1. Datta et al., at 2905. PKB signaling is also implicated in the physiological regulation of organ size (Verdu, et al., *Nat. Cell Biol.*, 1999, 1, 500-506), glucose homeostasis (Czech, et al., *J. Biol. Chem.*, 1999, 274, 1865-1868), vasomotor tone (Luo, et al. *J. Clin. Invest.* 1999, 106, 493-499), and angiogenesis (Kureishi, et al., *Nat. Med.*, 2000, 6, 1004-1010).

Manifestations of altered PKB regulation appear in both injury and disease, the most important role being in cancer. PKB kinase activity is constitutive activated in tumors with PTEN mutation, PI 3-kinase mutation and overexpression, and receptor tyrosine kinase overexpression. PKB is also a mediator of normal cell functions in response to growth factor signaling. Expression of the AKT gene was found to be amplified in 15% of human ovarian carcinoma cases. Cheng, et al., *Proc. Natl. Acad. Sci. U.S.A.*, 1992, 89, 9267-9271. AKT has also been found to be over expressed in 12% of pancreatic cancers. Cheng, et al., *Proc. Natl. Acad. Sci. U.S.A.*, 1996, 93, 3636-3641. In particular, AKT-2 is over-expressed in 12% of ovarian carcinomas and in 50% of undifferentiated tumors, suggesting that PKB may be associated with tumor aggressiveness. Bellacosa, et al., *Int. J. Cancer*, 1995, 64, 280-285. PKB is also a mediator of normal cell functions. Khwaja, *Nature*, 1999, 401, 33-34; Yuan, et al., *Oncogene*, 2000, 19, 2324-2330; Namikawa, et al., *J. Neurosci.*, 2000, 20, 2875-2886.

Elucidation of the role of PKB in the increase of growth and inhibition of apoptosis is complicated by the many protein substrates of PKB, including BAD, Forkhead (FOXO family), GSK3, Tuberin (TSC2), p27 Kip1, p70S6k, protein kinase C—, forkhead in rhabdomyosarcoma, Raf, cAMP-response element-binding protein, glycogen synthase kinase- 3, mTOR, and the androgen receptor. Lin, et al., *Proc. Natl. Acad. Sci. U.S.A.*, 2001, 98, 7200-7205; Blume-Jensen, et al., *Nature* 2001, 411, 355-365; Vivanco, et al., *Nat. Rev. Cancer,* 2002, 2, 489-501.

The various PKBs vary in their abundance in different mammalian cell types. For example, PKBβ are especially abundant in highly insulin-responsive tissues, including brown fat.

Modulation of PKB by small molecules can be achieved by identifying compounds that bind to and activate or inhibit one or more PKBs. Cao et al. in United States Publication No. 2004/0122016, published Jun. 24, 2004, disclose certain thiophene derivatives and thiophene analogs as inhibitors of protein kinases. In particular, the disclosure addresses compositions effective as inhibitors of Rho-associated coiled-coil forming protein serine/threonine kinase (ROCK), extracellular signal regulated kinase (ERK), glycogen synthase kinase (GSK), and members of the AGC sub-family of protein kinases. Id. at 4. The AGC sub-family of kinases includes protein kinase A (PKA), PDK, $p70^{S6K}$-1, $p70^{S6K}$-2, and PKB. Id.

Triciribine has been reported to inhibit cell growth in PBKβ overexpressing cells, transformed cells, and was effective at a concentration of 50 nM. Yang et al., *Cancer Res.*, 2004, 64, 4394-4399.

In other work, U.S. Pat. No. 3,904,756, issued Sep. 9, 1975, discloses substituted nitroimidazolyl thiadiazoles and oxadiazoles as antibacterial agents and growth promoting compounds. The patent does not address modulation of PKB.

U.S. Pat. No. 5,086,053, issued Feb. 4, 1992, discloses certain derivatives of 1,3,4-thiadiazole, a method of obtaining them, and pharmaceutical compositions containing them. The agents are described as muscarinic cholinergic agonists. Id. at col. 2, ll. 6-7. The '053 patent, however, does not disclose modulators of PKB.

Derivatives of 1,3,4-oxa(thia)diazolopyrimidin-5-ones, and related compounds, were synthesized. Yadav et al., *Synthesis*, 2003, 1, 63-66. Several derivatives of thiazolopyridopyrimidines and thiazolo-thiadiazolopyrimidines were synthesized by Singh and colleagues, and tested for antifungal activity. Singh et al., *Indian J. Chem.*, 1994, 33B, 350-354. Derivatives of 2-amino-1,3,4-thiadiazole, and related compounds, have been synthesized and tested for anesthetic activity. Mazzone et al., *Il Farmaco*, 1993, 48, 1207-1224. Some derivatives of thiadiazoles were synthesized and tested for antimicrobial activity. Pachhamia et al., *J. Inst. Chemists (India)*, 1989, 61, 54-56. Moreover, synthesis of acetamide derivatives of 1,3,4-thiadiazoles, and related compounds, have been reported. Shah et al., *J. Indian Chem. Soc.*, 1982, LIX, 678-680. None of the above references disclose modulation of PKB.

Anti-tumor effects of some 1,3,4-thiadiazole derivative(s) have been reported. Platonova, *Akad Med Nauk*, SSSR 2, 167, as cited by Shah et al. at 678.

4. SUMMARY OF THE INVENTION

This invention encompasses novel compounds useful for treating diseases or conditions mediated by PKB. The invention also encompasses the therapeutic use of such compounds and compositions thereof in the treatment of disease states associated with abnormal cell growth, such as cancer, or metabolic disease states, such as diabetes or inflammation.

In one aspect the invention comprises a compound of Formula I

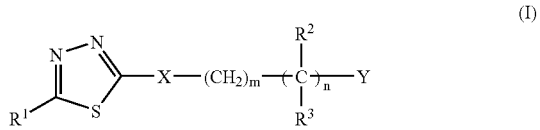

wherein:
Y is —N($R^4$)$R^5$ or —O$R^5$;
X is O, S, or N($R^6$);
$R^1$ is an aryl or heteroaryl;
$R^2$ and $R^3$ are each independently selected from the group consisting of $C_1$-$C_6$ alkyl which may be interrupted by one or more hetero atoms, —($CR^7R^8$)$_t$(aryl), —($CR^7R^8$)$_t$(heteroaryl), —($CR^7R^8$)$_t$(cycloalkyl), or —($CR^7R^8$)$_t$(heterocyclyl),
or $R^2$ is —H;
or $R^2$ and $R^3$ together with the carbon atom to which they are attached join to form a $C_3$-$C_{10}$ heterocyclic or carbocyclic ring system,
or $R^3$ and $R^6$ join to form a $C_3$-$C_{10}$ heterocyclic ring;
$R^4$ is —H, $C_1$-$C_8$ alkyl, —C(O)($CR^7R^8$)$_t$N($R^6$)$_2$, —C(O)($CR^7R^8$)$_t$, —C(O)$_2$($CR^7R^8$)$_t$, —($CR^7R^8$)$_t$(aryl), —(C $R^7R^8$)$_t$(heteroaryl), —($CR^7R^8$)$_t$(cycloalkyl), or —(C $R^7R^8$)$_t$(heterocyclyl),
or $R^4$ and $R^3$ join to form a $C_3$-$C_{10}$ heterocyclic ring;
$R^5$ and $R^6$ are independently selected from —H and $C_1$-$C_8$ alkyl, or $R^5$ and $R^6$ together with the atoms to which they are linked join to form a 5 to 6-membered heterocyclic ring, or $R^4$ and $R^5$ together with the nitrogen atom to which they are linked join to form a 5 to 6-membered heterocylic or heteroaryl ring; and
$R^7$ and $R^8$ are independently selected from —H, $C_1$-$C_6$ alkyl, and aryl;
wherein n is an integer from 1 to 6; m is an integer from 0 to 2; and each t is independently an integer from 0 to 3;
wherein each of the above alkyl, aryl, heteroaryl, cycloalkyl, heterocyclyl moieties and heterocyclic and carbocyclic rings are optionally and independently substituted by 1-3 substituents selected from
  amino,
  aryl, heteroaryl, cycloalkyl, or heterocyclyl optionally substituted by 1-5 substituents selected from
    $C_1$-$C_6$ alkoxy,
    $C_1$-$C_6$ alkyl optionally substituted by halo,
    aryl,
    halo,
    heteroaryl,
    $C_1$-$C_6$ hydroxyl, and
    —NHS(O)$_2$—$C_1$-$C_6$ alkyl);
  $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamino,
  $C_2$-$C_6$ alkenyl, or $C_2$-$C_6$ alkynyl, wherein each of which may be interrupted by one or more hetero atoms,
  cyano,
  halo,
  hydroxy,
  nitro, or
  —O-aryl;
or a pharmaceutically acceptable salt, hydrate, or stereoisomer thereof.

In one embodiment the invention comprises a compound of Formula I wherein m, n, and t are 1.

In another embodiment the invention comprises a compound of Formula I wherein X is —N($R^6$) and Y is —N($R^4$)($R^5$).

In another embodiment the invention comprises a compound of Formula I wherein X is —N(R$^6$), Y is —N(R$^4$)(R$^5$), R$^1$ is heteroaryl, R$^2$ is —H, R$^3$ is —(CR$^7$R$^8$)$_t$(aryl) or —(CR$^7$R$^8$)$_t$(heteroaryl), and m, n, and t are 1.

In another embodiment the invention comprises a compound of Formula I wherein X is —N(R$^6$), Y is —N(R$^4$)(R$^5$), R$^1$ is heteroaryl, R$^2$ is —H, R$^3$ is —(CR$^7$R$^8$)$_t$(aryl) or —(CR$^7$R$^8$)$_t$(heteroaryl), and m, n, and t are 1, wherein R$^4$, R$^5$, and R$^6$ are —H, and R$^7$ and R$^8$ are independently selected from H and C$_1$-C$_3$ alkyl.

In another embodiment, the invention comprises a compound of Formula I selected from
(S)-3-(3-Fluoro-phenyl)-N-[5-(3-methyl-1H-indazol-5-yl)-[1,3,4]thiadiazol-2-yl]-propane-1,2-diamine;
(S)-3-(3,4-Difluoro-phenyl)-N-[5-(3-methyl-1H-indazol-5-yl)-[1,3,4]thiadiazol-2-yl]-propane-1,2-diamine;
(S)-3-(3,4-Dichloro-phenyl)-N-[5-(3-methyl-H-indazol-5-yl)-[1,3,4]thiadiazol-2-yl]-propane-1,2-diamine;
N—((S)-2-amino-3-(4-(trifluoromethyl)phenyl)propyl)-5-(3-methyl-1H-indazol-5-yl)-1,3,4-thiadiazol-2-amine;
N—((S)-2-amino-3-(2-bromophenyl)propyl)-5-(3-methyl-1H-indazol-5-yl)-1,3,4-thiadiazol-2-amine;
N—((S)-2-amino-3-(4-ethylphenyl)propyl)-5-(3-methyl-1H-indazol-5-yl)-1,3,4-thiadiazol-2-amine;
N—((S)-2-amino-3-(3,5-difluorophenyl)propyl)-5-(3-methyl-1H-indazol-5-yl)-1,3,4-thiadiazol-2-amine;
N—((S)-2-amino-3-(2-methoxyphenyl)propyl)-5-(3-methyl-1H-indazol-5-yl)-1,3,4-thiadiazol-2-amine;
(S)-3-(4-Methoxy-phenyl)-N-[5-(3-methyl-1H-indazol-5-yl)-[1,3,4]thiadiazol-2-yl]-propane-1,2-diamine;
(S)-3-(2-Chloro-phenyl)-N-[5-(3-methyl-1H-indazol-5-yl)-[1,3,4]thiadiazol-2-yl]-propane-1,2-diamine;
(S)—N-[5-(3-Methyl-1H-indazol-5-yl)-[1,3,4]thiadiazol-2-yl]-3-o-tolyl-propane-1,2-diamine;
(S)—N-[5-(3-Methyl-1H-indazol-5-yl)-[1,3,4]thiadiazol-2-yl]-3-(3-trifluoromethyl-phenyl)-propane-1,2-diamine;
(S)-3-(4-Fluoro-phenyl)-N-[5-(3-methyl-1H-indazol-5-yl)-[1,3,4]thiadiazol-2-yl]-propane-1,2-diamine;
(S)-3-(4-Chloro-phenyl)-N-[5-(3-methyl-1H-indazol-5-yl)-[1,3,4]thiadiazol-2-yl]-propane-1,2-diamine;
(S)—N-[5-(3-Methyl-1H-indazol-5-yl)-[1,3,4]thiadiazol-2-yl]-3-m-tolyl-propane-1,2-diamine;
N—((S)-2-amino-3-(3-bromophenyl)propyl)-5-(3-methyl-1H-indazol-5-yl)-1,3,4-thiadiazol-2-amine;
N—((S)-2-amino-3-(3-chlorophenyl)propyl)-5-(3-methyl-1H-indazol-5-yl)-1,3,4-thiadiazol-2-amine;
N—((S)-2-amino-3-(4-isopropylphenyl)propyl)-5-(3-methyl-H-indazol-5-yl)-1,3,4-thiadiazol-2-amine;
N—((S)-2-amino-3-(2,4-dichlorophenyl)propyl)-5-(3-methyl-H-indazol-5-yl)-1,3,4-thiadiazol-2-amine;
N—((S)-2-amino-3-p-tolylpropyl)-5-(3-methyl-1H-indazol-5-yl)-1,3,4-thiadiazol-2-amine;
N—((S)-2-amino-3-(naphthalen-2-yl)propyl)-5-(3-methyl-1H-indazol-5-yl)-1,3,4-thiadiazol-2-amine;
N—((S)-2-amino-3-(benzo[b]thiophen-3-yl)propyl)-5-(3-methyl-H-indazol-5-yl)-1,3,4-thiadiazol-2-amine;
N—((S)-2-amino-3-(4-chlorophenyl)propyl)-5-(1H-indazol-5-yl)-1,3,4-thiadiazol-2-amine;
N—((S)-2-amino-3-(4-(trifluoromethyl)phenyl)propyl)-5-(1H-indazol-5-yl)-1,3,4-thiadiazol-2-amine;
N—((S)-2-amino-3-(naphthalen-2-yl)propyl)-5-(1H-indazol-5-yl)-1,3,4-thiadiazol-2-amine;
N—((S)-2-amino-3-(4-isopropylphenyl)propyl)-5-(1H-indazol-5-yl)-1,3,4-thiadiazol-2-amine;
N—((S)-2-amino-3-(3,4-dichlorophenyl)propyl)-5-(1H-indazol-5-yl)-1,3,4-thiadiazol-2-amine;
N—((S)-2-amino-3-(2,4-dichlorophenyl)propyl)-5-(1H-indazol-5-yl)-1,3,4-thiadiazol-2-amine;
N—((S)-2-amino-3-(4-methoxyphenyl)propyl)-5-(1H-indazol-5-yl)-1,3,4-thiadiazol-2-amine;
N—((S)-2-amino-3-(4-bromophenyl)propyl)-5-(1H-indazol-5-yl)-1,3,4-thiadiazol-2-amine;
N—((S)-2-amino-3-(3-(trifluoromethyl)phenyl)propyl)-5-(1H-indazol-5-yl)-1,3,4-thiadiazol-2-amine;
N—((S)-2-amino-3-(3-(trifluoromethyl)phenyl)propyl)-5-(3-methyl-1H-pyrazolo[3,4-b]pyridin-5-yl)-1,3,4-thiadiazol-2-amine;
N—((S)-3-(4-chlorophenyl)-2-(methylamino)propyl)-5-(3-methyl-1H-indazol-5-yl)-1,3,4-thiadiazol-2-amine;
5-(3-methyl-1H-indazol-5-yl)-N—((S)-2-(methylamino)-3-(3-(trifluoromethyl)phenyl)propyl)-1,3,4-thiadiazol-2-amine;
5-(1H-indazol-5-yl)-N—((S)-2-(methylamino)-3-(4-(trifluoromethyl)phenyl)propyl)-1,3,4-thiadiazol-2-amine;
N—((S)-2-amino-3-(4-methoxyphenyl)propyl)-5-(isoquinolin-6-yl)-1,3,4-thiadiazol-2-amine;
N—((S)-2-amino-3-(3-(trifluoromethyl)phenyl)propyl)-5-(isoquinolin-6-yl)-1,3,4-thiadiazol-2-amine;
N—((S)-2-amino-3-(4-(trifluoromethyl)phenyl)propyl)-5-(isoquinolin-6-yl)-1,3,4-thiadiazol-2-amine;
N—((S)-2-amino-3-(3-methoxyphenyl)propyl)-5-(isoquinolin-6-yl)-1,3,4-thiadiazol-2-amine;
N—((S)-2-amino-3-(2,4-dichlorophenyl)propyl)-5-(isoquinolin-6-yl)-1,3,4-thiadiazol-2-amine;
N—((S)-2-amino-3-(4-dichlorophenyl)propyl)-5-(isoquinolin-6-yl)-1,3,4-thiadiazol-2-amine;
N—((S)-2-amino-3-(3,5-difluorophenyl)propyl)-5-(isoquinolin-6-yl)-1,3,4-thiadiazol-2-amine;
N—((S)-2-amino-3-m-tolylpropyl)-5-(isoquinolin-6-yl)-1,3,4-thiadiazol-2-amine;
N—((S)-2-amino-3-(4-(trifluoromethyl)phenyl)propyl)-5-(1,6-naphthyridin-2-yl)-1,3,4-thiadiazol-2-amine;
N—((S)-2-amino-3-(4-bromophenyl)propyl)-5-(3-methyl-1H-indazol-5-yl)-1,3,4-thiadiazol-2-amine;
N-((2S,3S)-2-amino-3-(4-(trifluoromethyl)phenyl)butyl)-5-(isoquinolin-6-yl)-1,3,4-thiadiazol-2-amine; and
N-((2S,3S)-2-amino-3-(4-(trifluoromethyl)phenyl)butyl)-5-(1H-indazol-5-yl)-1,3,4-thiadiazol-2-amine.

In another aspect, the invention comprises a pharmaceutically acceptable salt, hydrate, or solvate of a compound of Formula I. In one embodiment, the pharmaceutically acceptable salts of Formula I compounds are selected from ammonium trifluoroacetate and ammonium chloride.

In another aspect, the invention comprises a pharmaceutical composition comprising a pharmaceutically-acceptable carrier and a compound of Formula I.

In another aspect, the invention comprises a method for treating a kinase-mediated disorder in a mammal comprising administering to the mammal a therapeutically effective amount of a compound of Formula I. The disorder can be one that is mediated by PKA, PKB, PKC, FKHR, SGK, LCK, BTK, Tie2, KDR, Erk, MSK, MK2, MSK, p38, P70S6, ROCK2, GSK3 or a CDK complex.

In another embodiment, the invention encompasses Formula I compounds that have selective kinase activity—i.e., they possess significant activity against one specific kinase while possessing less or minimal activity against a different kinase.

Another embodiment of the invention comprises treating abnormal cell growth by administering a therapeutically effective amount of a compound of the invention to a subject in need thereof. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

In another embodiment, the invention comprises a method of administering a therapeutically effective amount of a Formula I compound to a mammal for treating disease states or conditions selected from diabetes, inflammation, and metabolic disorders.

In another embodiment, the invention encompasses a method for treating or preventing cancer in a patient in need thereof, comprising administering to the patient a therapeutically or prophylactically effective amount of a compound according to Formula I and a pharmaceutically acceptable excipient, carrier, or vehicle.

In another aspect, the invention encompasses a method for treating or preventing cancer in a patient in need thereof, comprising administering to the patient a therapeutically or prophylactically effective amount of a Formula I compound and at least one additional therapeutic agent.

5. DETAILED DESCRIPTION OF THE INVENTION

5.1 Definitions

Where the following terms are used in this specification, they are used as defined below:

The terms "comprising" and "including" are used herein in their open, non-limiting sense.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-me-thylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-dimethylpentyl, 3,3-diethylhexyl, 2,2-diethylhexyl, 3,3-diethylhexyl and the like. An alkyl group can be unsubstituted or substituted.

As used herein, unless otherwise specified, the term "alkenyl" means an unsaturated straight chain or branched non-cyclic hydrocarbon having from 2 to 20 carbon atoms and at least one carbon-carbon double bond. Preferably an alkenyl has 2 to 10 carbon atoms and most preferably 2 to 4 carbon atoms. Exemplary straight chain alkenyls include -but-3-ene, -hex-4-ene, and -oct-1-ene. Exemplary branched chain alkenyls include -2-methyl-obut-2-ene, -1-methyl-hex-4-ene, and -4-ethyl-oct-1-ene. An alkenyl group can be substituted or unsubstituted.

As used herein, and unless otherwise specified, the term "alkynyl" means an alkyl group in which one or more carbon-carbon single bonds is replaced with an equivalent number of carbon-carbon triple bonds. An alkynyl group must comprise at least two carbon atoms, and can be substituted or unsubstituted.

As used herein, unless otherwise specified, the term "haloalkyl" means an alkyl group in which one or more hydrogens has been replaced by a halogen atom. A halogen atom is a fluorine, chlorine, bromine, or iodine atom.

As used herein, unless otherwise specified, the term "hydroxyalkyl" means an alkyl group in which one or more hydrogens has been replaced with a hydroxyl group.

The term "alkoxy" means a structure of the formula —O-alkyl.

The term "alkylsulfonyl" means a structure of the formula —S(O)$_2$-alkyl.

The terms "alkylamine" and "dialkylamino" mean a structure of the formula —N-alkyl and —NH(alkyl)alkyl, respectively, wherein the alkyl is defined as above.

The term "alkanoyl", alone or in combination with another term, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like. The terms "alkanoylamino" and "alkanoyloxy" mean —NH-alkanoyl and —O-alkanoyl, respectively.

The term "alkoxy carbonyl amino" means a structure of the formula —NHC(O)O-alkyl.

The term "alkylsulfonyl amino" means a structure of the general formula —NHS(O)$_2$-alkyl.

As used herein, unless otherwise specified the term "aryl" means a carbocyclic ring or ring system containing from 5 to 14 ring atoms wherein at least one ring is aromatic. The ring atoms of a carbocyclic aryl group are all carbon atoms. Aryl groups include mono-, bi-, or tricyclic groups as well as benzo-fused carbocyclic moieties such as 5,6,7,8-tetrahydronaphthyl and the like. Preferably, the aryl group is a monocyclic ring or bicyclic ring. Representative aryl groups include phenyl, tolyl, anthracenyl, fluorenyl, indenyl, azulenyl, phenanthrenyl and naphthyl. An aryl group can be unsubstituted or substituted.

The term "heteroaryl" means an aryl group in which one or more, but not all, of the ring carbon atoms is substituted by a hetero atom. Exemplary heteroatoms are N, O, S, and Si. A heteroaryl group can be unsubstituted or substituted.

The term "cycloalkyl" means an unsaturated or saturated hydrocarbon that forms at least one ring, having from 3 to 20 ring carbon atoms, preferably from 3 to 10 ring carbon atoms. The rings in a cycloalkyl group are not aromatic. A cycloalkyl group can be unsubstituted or substituted.

The term "heterocyclyl" means a cycloalkyl in which at least one but not all ring carbon atoms is substituted by a heteroatom. Exemplary heteroatoms are NH, O, and S.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "PKB" refers to protein kinase B, also known as AKT.

The term "treating" refers to:

(i) preventing a disease, disorder, or condition from occurring in a mammal that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition, or one or more of its symptoms.

The term "preventing" refers to the ability of a compound or composition of the invention to prevent a disease identified herein in mammals diagnosed as having the disease or who are at risk of developing such disease. The term also encompasses preventing further progression of the disease in mammals who are already suffering from or have symptoms of such disease.

The term "mammal" refers to non-human animals or humans.

As used herein, the term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of a cancer, the term "patient" or "subject" preferably means a monkey or a human, most preferably a human. In a specific embodiment the patient or subject is afflicted by a cancer.

As used herein, a "therapeutically effective amount" refers to an amount of a Formula I compound of the invention, or prodrug thereof, sufficient to provide a benefit in the treatment or prevention of a condition or disease such as cancer, to delay or minimize symptoms associated with the condition or disease, or to cure or ameliorate the disease or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

As used herein, a "prophylactically effective amount" refers to an amount of a compound of the invention or other active ingredient sufficient to result in the prevention of a condition or disease such as cancer, or recurrence or metastasis of cancer. A prophylactically effective amount may refer to an amount sufficient to prevent initial disease or the recurrence or spread of the disease. The term preferably encompasses a non-toxic amount that improves overall prophylaxis or enhances the prophylactic efficacy of or synergies with another prophylactic or therapeutic agent.

As used herein, "in combination" refers to the use of more than one prophylactic and/or therapeutic agents simultaneously or sequentially. The agents may be selected and administered in such a manner that their respective effects are additive or synergistic.

As used herein, the term "pharmaceutically acceptable salts" refers to salts prepared from pharmaceutically acceptable non-toxic acids or bases including inorganic and organic acids and bases. If the Formula I compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the Formula I compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The term "prodrug" is intended to mean any chemical entity that after administration is converted to a different therapeutically effective chemical entity.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

As used herein and unless otherwise indicated, the term "optically pure" or "stereomerically pure" means a composition that comprises one stereoisomer of a compound and is substantially free of other stereoisomers of that compound. For example, a stereomerically pure compound having one chiral center will be substantially free of the opposite enantiomer of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The compounds of the invention may exhibit the phenomenon of tautomerism. While Formula I cannot expressly depict all possible tautomeric forms, it is to be understood that Formula I is intended to represent any tautomeric form of the depicted compound and are not to be limited merely to a specific compound form depicted by the formula drawings.

5.2 Methods of Treatment and Prevention of Disease States Mediated by PKB Activity The present invention provides methods for treating or preventing PKB-mediated disease states, such as cancer.

5.2.1 Doses

The magnitude of a prophylactic or therapeutic dose of a Formula I compound of the invention, or a pharmaceutically acceptable salt, solvate, hydrate, or stereoisomer thereof, in the acute or chronic treatment or prevention of a disease or condition such as abnormal cell growth or cancer will vary with the nature and severity of the disease, and the route by which the active ingredient is administered. The dose, and in some cases the dose frequency, will also vary according to the abnormal cell growth to be treated, the age, body weight, and response of the individual patient. Suitable dosing regimens can be readily selected by those skilled in the art with due consideration of such factors.

The magnitude of a prophylactic or therapeutic dose of a Formula I compound of the invention or a pharmaceutically acceptable salt, solvate, hydrate, or stereoisomer thereof in the acute or chronic treatment or prevention of a cancer or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. In a related embodiment, the compounds of the invention are administered to produce a systemic effect in the body.

In another embodiment, the compounds of the invention are administered directly to the site affected by the condition, as, for example, an accessible skin or esophageal cancer.

In another embodiment the compounds of the invention are administered via oral, mucosal (including sublingual, buccal, rectal, nasal, or vaginal), parenteral (including subcutaneous, intramuscular, bolus injection, intra-arterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In a further specific embodiment, the compounds of the invention are administered via oral administration. In an alternative specific embodiment, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

5.2.2 Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, anti-emetic agents, antidepressants, and antifungal agents, anti-inflammatory agents, antiviral agents, other anticancer agents, immunomodulatory agents, alpha-interferons, β-interferons, alkylating agents, hormones or cytokines. In a preferred embodiment the invention encompasses the administration of an additional therapeutic agent that demonstrates anti-cancer activity.

The compounds of the invention and the other therapeutics agent can act additively or, preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent.

In one embodiment, the methods of the invention comprise the administration of one or more Formula I compounds of the invention without an additional therapeutic agent.

5.3 Pharmaceutical Compositions and Dosage Forms

Pharmaceutical compositions and single unit dosage forms comprising a Formula I compound of the invention, or a pharmaceutically acceptable salt, hydrate, metabolite or stereoisomer thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intra-arterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a Formula I compound of the invention, or a pharmaceutically acceptable salt, hydrate or stereoisomer thereof, and at least one additional therapeutic agent. Examples of additional therapeutic agents include, but are not limited to, those listed above in Section 4.2.2.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 20th ed., Mack Publishing, Easton Pa. 2000. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms particularly suitable for parenteral administration to a patient; and sterile solids (e.g., crystalline or amorphous solids) that can be reconstituted to provide liquid dosage forms suitable for parenteral administration to a patient.

Like the amounts and types of excipients, the amounts and specific types of active ingredients in a dosage form may differ depending on factors such as, but not limited to, the route by which it is to be administered to patients. However, typical dosage forms of the invention comprise Formula I compounds of the invention, or a pharmaceutically acceptable salt, hydrate, or stereoisomers thereof comprise 0.1 mg to 1500 mg per unit to provide doses of about 0.01 to 200 mg/kg per day.

The foregoing demonstrates the pertinent and important features of the present invention. One of skill in the art will appreciate that numerous modifications and embodiments thereof may be devised. Therefore, it is intended that the appended claims cover all such modifications and embodiments.

6. Working Examples

The compounds of Formula I were prepared according to the following synthetic schemes and individual examples detailed therein. The compounds were named using Chemdraw Ultra, v.8.07. These schemes and examples are provided for the purpose of illustration only and are not intended as limiting the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company. All reactions involving air- or moisture-sensitive compounds were performed under a nitrogen atmosphere. Flash chromatography was performed using Aldrich Chemical Company silica gel (200-400 mesh, 60 A) or Biotage pre-packed column. Thin-layer chromatography (TLC) was performed with Analtech gel TLC plates (250 mµ.). Preparative TLC was performed with Analtech silica gel plates (1000-2000.mu.). Preparative HPLC was conducted on a Beckman or Waters HPLC system with 0.1% $TFA/H_2O$ and 0.1% $TFA/CH_3CN$ as mobile phase. The flow rate was at 20 mL/min. and gradient method was used. $^1H$ NMR spectra were determined with super conducting FT NMR spectrometers operating at 400 MHz or a Varian 300 MHz instrument. Chemical shifts are expressed in ppm downfield from internal standard tetramethylsilane. All compounds showed NMR spectra consistent with their assigned structures. Mass spectra (MS) were determined on a Perkin Elmer-SCIEX API 165 electrospray mass spectrometer (positive and/or negative) or an HP 1100 MSD LC-MS with electrospray ionization and quadrupole detection. All parts are by weight and temperatures are in Degrees centigrade unless otherwise indicated.

The following abbreviations are used: AcOH or HOAc (acetic acid), $Ac_2O$ (acetic anhydride), $Al_2O_3$ (alumina), AIBN (2,2'-azobisisobutyronitrile), Ar (argon), $AgSO_4$ (silver sulfate), ATP (adenosine triphosphate), 9-BBN (9-borabicyclo[3.3.1]nonane), $BH_3$ (borane), BINAP (2,2'-bis(diphenylphosphino)-1,1'-binaphthyl), Boc (tert-butyloxycarbonyl), $Boc_2O$ (Boc anhydride), BOP-Cl (bis(2-oxo-3-oxazolidinyl)phosphinic chloride), $Br_2$ (bromine), BSA (bovine serum albumin), t-BuOH (tert-butanol), CAN (ammonium cerium(IV) nitrate), $CH_3CN$ or AcCN (acetonitrile), $CH_2Cl_2$ (dichloromethane), $CH_3I$ or MeI (iodomethane or methyl iodide), $CCl_4$ (carbon tetrachloride), $CCl_3$ (chloroform), $CO_2$ (carbon dioxide), $Cs_2CO_3$ (cesium carbonate), DIEA (diisopropylethylamine), CuI (copper iodide), DCE (1,2-dichloroethane), DEA (diethylamine), DEAD (diethyl azodicarboxylate), DIEA (diisopropylethylamine), dppf (1,1-diphenylphosphinoferrocene), DMAP (4-(dimethylamino)pyridine), DMAC (N,N-dimethylacetamide), DMF (dimethylformamide), DMSO (dimethylsulfoxide), DTT (dithiothreitol), EDC or EDAC, 1-(3-dimethylaminopropyl)-3 (ethylcarbodiimide hydrochloride), EGTA (ethylene glycol-bis($\beta$-aminoethyl ether)), N,N,N',N' (tetraacetic acid), EtOAc (ethyl acetate), EtOH (ethanol), $Et_2O$ (diethyl ether), Fe (iron), g (gram), h (hour), HATU (O-(7-azabenzotriazol-1-yl)-N,N,N',N' (tetramethyluronium) hexafluorophosphate), $H_2$ (hydrogen), $H_2O$ (water), HCl (hydrochloric acid), $H_2SO_4$ (sulfuric acid), $H_2NNH_2$ (hydrazine), $HC(OEt)_3$ (triethylorthoformate), HCHO or $H_2CO$ (formaldehyde), HCOOH (formic acid), $HCO_2Na$ (sodium formate), HOAc, AcOH (acetic acid), HOAt (1-hydroxy-7-azabenzotriazole), HOBt (hydroxybenzotriazole), ipOH, i-PrOH (isopropanol), $K_2CO_3$ (potassium carbonate), KHMDS (potassium hexamethylsilazane), $KNO_3$ (potassium nitrate), KOAc (potassium acetate), KOH (potassium hydroxide), LAH or $LiAlH_4$ (lithium aluminum hydride), LDA (lithium diisopropylamide), LiCl (lithium chloride), LiHMDS (lithium hexamethyldisilazide), LiOH (lithium hydroxide), $LiN(TMS)_2$ (lithium bis(trimethylsilyl)amide), MeOH (methanol), $MgCl_2$ (magnesium chloride), $NgSO_4$ (magnesium sulfate), mg (milligram), min (minute), mL (milliliter), $NnCl_2$ (manganese chloride), NBS (N-bromosuccinimide), NMO (4-methylmorpholine), N-oxide, NMP (N-methylpyrrolidone), $Na_2SO_4$ (sodium sulfate), $Na_2S_2O_5$ (sodium metabisulfite), $NaHCO_3$ (sodium bicarbonate), $Na_2CO_3$ (sodium carbonate), NaCl (sodium chloride), NaH (sodium hydride), NaI (sodium iodide), NaOH (sodium hydroxide), NaOMe (sodium methoxide), NaOtBu (sodium tert-butoxide), $NaCNBH_3$ (sodium cyanoborohydride), $NaBH_4$ (sodium borohydride), $NaNO_2$ (sodium nitrate), $NaBH(OAc)_3$ (sodium triacetoxyborohydride), $NH_4Cl$ (ammonium chloride), $N_2$ (nitrogen), Pd/C (palladium on carbon), $PdCl_2$, $(PPh_3)_2$ (palladium chloride bis(triphenylphosphine)), $Pd_2(dba)_3$ (palladium dibenzylideneacetone), $PdCl_2(dppf)$ (1,1-bis(diphenylphosphino)ferrocene, palladium chloride), $Pd(PPh_3)_4$ (palladium tetrakis triphenylphosphine), $Pd(OH)_2$ (palladium hydroxide), $Pd(OAc)_2$ (palladium acetate), PMB (para methoxybenzyl), $POCl_3$ (phosphorus oxychloride), $PPh_3$ (triphenylphosphine), $PtO_2$ (platinum oxide), RT (room temperature), $SiO_2$ (silica), $SOCl_2$ (thionyl chloride), TBAI (tetrabutylammonium iodide), TBTU (O-(1H-Benzatriazol-1-yl)), N,N,N,N (tetramethyluronium) tetrafluoroborate), TEA (triethylamine), $Tf_2NPh$ (N-phenyltrifluoromethanesulfonimide), TFA (trifluoroacetic acid), THF (tetrahydrofuran), TPAP (tetrapropylammoniumperruthenate), Tris-HCl (Tris(hydroxymethyl)aminomethane hydrochloride salt), and Zn (zinc).

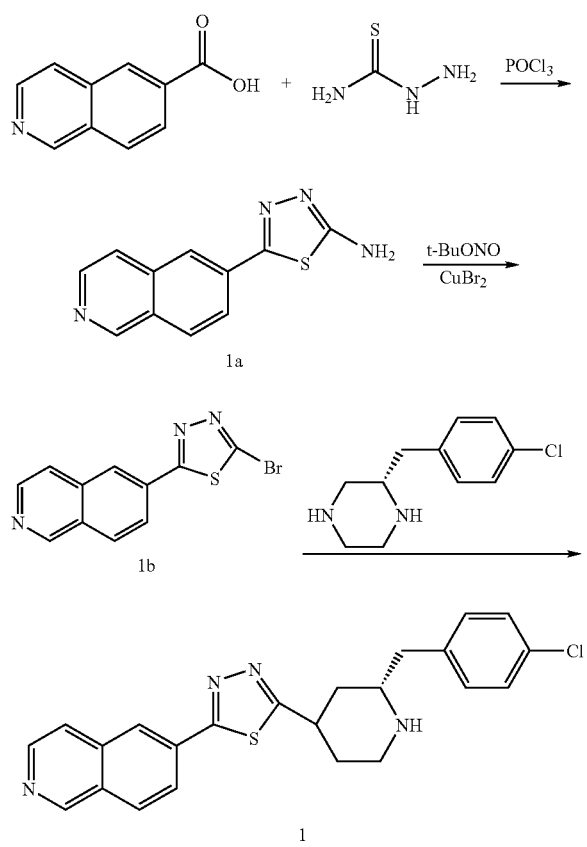

5-Isoquinolin-6-yl-[1,3,4]thiadiazol-2-ylamine (1a): Commercially available isoquinoline-6-carboxylic acid (15.4 g, 89 mmol) and thiosemicarbazide (12.2 g, 133 mmol) were mixed in 150 ml phosphorus oxychloride. The mixture was heated at 80° C. for 60 hours. After removing the excess phosphorus oxychloride via rotatory evaporation at a reduced pressure, the remaining residue was mixed with ice water and the pH increased to pH 12 with KOH. After filtration and washing with water, a yellow amorphous solid 1a was obtained as the crude product (17 g, y (yield)=85%). It was used directly for next step. A pure sample of the product was obtained by subjecting the crude product to a silica gel column chromatography with a gradient of 1-5% 2M $NH_3$ methanol solution in dichloromethane as the eluent. $^1H$ NMR (400 MHz, DMSO-$d_6$): δ 7.73 (s, 2H), 8.02 (d, J=6 Hz, 1H), 8.27 (m, 2H), 8.38 (s, 1H), 8.66 (d, J=6 Hz, 1H), 9.45 (s, 1H). MS (API-ES) m/z (%): 229 (100%, $M^++1$).

6-(5-Bromo-[1,3,4]thiadiazol-2-yl)-isoquinoline (1b): tert-Butyl nitrite (1.95 g, 18.9 mmol) and copper(II) bromide (3.38 g, 15.1 mmol) were heated in 50 ml acetonitrile to 60° C. in a round bottom flask. 5-Isoquinolin-6-yl-[1,3,4]thiadiazol-2-ylamine (1a) was finely suspended in 100 ml acetonitrile. The suspension was added dropwise into the heated round bottom flask and the resulting mixture was heated at 70° C. for 1.5 hours. The reaction mixture was concentrated to 30 ml at a reduced pressure and mixed with 100 ml 20% HBr aqueous solution. The resulting mixture was allowed to stand in a freezer (−20° C.) for 12 hours. After filtration, washing the filtrate cake with 10% HBr aqueous solution, then water, dried via vacuum, a greenish solid (3.7 g, y=79%) was obtained as the HBr salt of the desired product. MS (API-ES) m/z (%): 292 (100%, $M^++1$), 294(100%, $M^++3$). The crude product was used directly for the next step.

Example 1

6-(5-((S)-3-(4-chlorobenzyl)-piperazin-1-yl)-1,3,4-thiadiazol-2-yl)-isoquinoline (1). Compound 1b (0.31 g, 0.83 mmol), S-2-(4-chloro-benzyl)-piperazine (0.23 g, 1.10 mmol), diisopropylethylamine (0.58 ml, 3.33 mmol) and 1.5 ml N-methylpyrrolidinone were mixed in a 2 ml microwave heating vial. The mixture was heated under microwave at 180° C. for 40 minutes. The reaction mixture was partitioned between ethylacetate and saturated aqueous sodium bicarbonate. After removing the ethylacetate, the crude product was subjected to a silica gel column and a HPLC chromatography to yield a yellow amorphous solid as the pure product (0.16 g, y=46%). $^1H$ NMR (400 MHz, $CDCl_3$): δ 2.67 (m, 1H), 2.84 (m, 1H), 2.95 (m, 1H), 3.12 (m, 2H), 3.38 (m, 1H), 3.86 (d, J=12.8 Hz, 1H), 4.01 (d, J=10.4 Hz, 1H), 7.17 (d, J=8.0 Hz, 2H), 7.30 (d, J=8.0 Hz, 2H), 7.67 (d, J=6.0 Hz, 1H), 8.01 (d, J=8.8 Hz, 1H), 8.09 (s, 1H), 8.16 (d, J=8.8 Hz, 1H), 8.55 (d, J=6.0 Hz, 1H), 9.25 (s, 1H); MS (API-ES) m/z (%): 422 (100%, $M^++1$).

Example 2

N—((S)-2-amino-3-phenylpropyl)-5-(isoquinolin-6-yl)-1,3,4-thiadiazol-2-amine (2). The compound was synthesized in a way similar to example 1 and purified by reverse phase HPLC as a TFA salt: $^1H$ NMR (400 MHz, Methanol-$d_4$): δ 3.08 (m, 2H), 3.71 (m, 1H), 3.83 (m, 1H), 3.91 (m, 1H), 7.38 (m, 5H), 8.50-8.60 (m, 5H), 9.75 (s, 1H), MS (API-ES) m/z (%): 363 (100%, $M^++1$); HRMS (ESI): calculated for C20H19N5S [M+1]: 362.1439; found: 362.1424.

Scheme 2

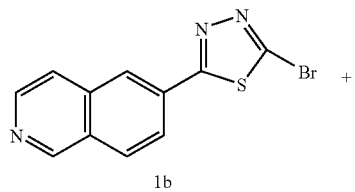

3.12 (m, 1H), 3.58 (m, 2H), 3.74 (m, 1H), 7.33 (t, J=7.2 Hz, 1H), 7.41 (t, J=7.2 Hz, 1H), 7.69 (d, J=7.6 Hz, 1H), 8.32 (m, 2H), 8.46 (d, J=8.8 Hz, 1H), 8.53 (m, 2H), 8.72 (s, 1H), 9.60 (s, 1H); MS (API-ES) m/z (%): 402 (95%, M$^+$+1), 424 (100%, M+Na$^+$); HRMS (ESI): calculated for C22H19N5OS [M+1]: 402.1388; found: 402.1394.

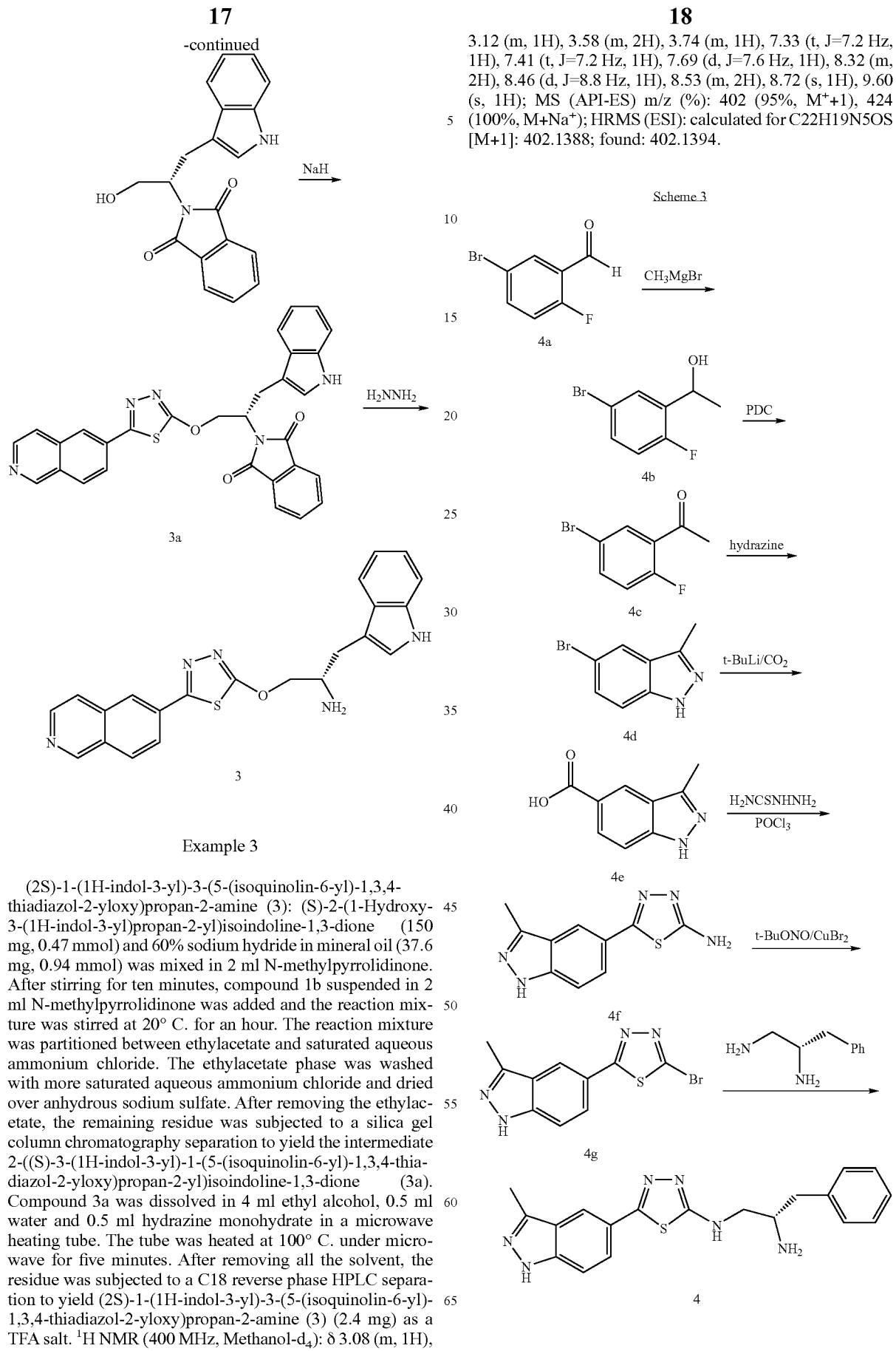

Example 3

(2S)-1-(1H-indol-3-yl)-3-(5-(isoquinolin-6-yl)-1,3,4-thiadiazol-2-yloxy)propan-2-amine (3): (S)-2-(1-Hydroxy-3-(1H-indol-3-yl)propan-2-yl)isoindoline-1,3-dione (150 mg, 0.47 mmol) and 60% sodium hydride in mineral oil (37.6 mg, 0.94 mmol) was mixed in 2 ml N-methylpyrrolidinone. After stirring for ten minutes, compound 1b suspended in 2 ml N-methylpyrrolidinone was added and the reaction mixture was stirred at 20° C. for an hour. The reaction mixture was partitioned between ethylacetate and saturated aqueous ammonium chloride. The ethylacetate phase was washed with more saturated aqueous ammonium chloride and dried over anhydrous sodium sulfate. After removing the ethylacetate, the remaining residue was subjected to a silica gel column chromatography separation to yield the intermediate 2-((S)-3-(1H-indol-3-yl)-1-(5-(isoquinolin-6-yl)-1,3,4-thiadiazol-2-yloxy)propan-2-yl)isoindoline-1,3-dione (3a). Compound 3a was dissolved in 4 ml ethyl alcohol, 0.5 ml water and 0.5 ml hydrazine monohydrate in a microwave heating tube. The tube was heated at 100° C. under microwave for five minutes. After removing all the solvent, the residue was subjected to a C18 reverse phase HPLC separation to yield (2S)-1-(1H-indol-3-yl)-3-(5-(isoquinolin-6-yl)-1,3,4-thiadiazol-2-yloxy)propan-2-amine (3) (2.4 mg) as a TFA salt. $^1$H NMR (400 MHz, Methanol-d$_4$): δ 3.08 (m, 1H), 5-bromo-2-fluoro-phenyl-ethanol (4b): Commercially available 4a (150.0 g, 739 mmol) was charged into a 2 liter round bottom flask. The reaction mixture in the flask was immersed in an ice-water bath. Methylmagnesium bromide (270 ml, 812 mmol) was added dropwise via an additional funnel. The reaction mixture was continually stirred for one more hour after the addition. After the reaction was completed, the mixture was slowly poured into 500 ml ice water plus 250 ml saturated ammonium chloride. The resulting aqueous solution was extracted with ether (800 ml×2) in a separation funnel. The combined ether layer was washed with brine and dried over sodium sulfate. Removal of the solvent gave the product (4b) (150 g, yield=93%). The product was used directly for the next step without further purification.

1-(5-bromo-2-fluoro-phenyl)-ethanone (4c): Compound 4b (50.0 g, 228 mmol) along with 300 ml dichloromethane was charged into 2 liter round bottom flask. Crushed pyridinium dichromate (171.0 g, 456 mmol) and powdered molecular sieves (10 g) were both added into the flask. The heterogeneous reaction mixture was stirred for 16 hours at 20° C. The resulting reaction mixture was filtered through celite and washed with ether (500 ml×3). The combined filtrate was concentrated under reduced pressure. The crude product was eluted through a short silica gel pad (3 inches in length) with 10% EtOAc in hexane. The resulting product (42.0 g, yield=84%) was used for the following step.

5-bromo-3-methyl-1H-indazole (4d): Compound (4c) (66.0 g, 304 mmol) and 350 ml anhydrous hydrazine were charged into a 1 Liter round bottom flask. The resulting reaction mixture was refluxed at 117° C. for 5 hours. After the reaction mixture was allowed to cool down to room temperature, the excess hydrazine was evaporated under reduced pressure to yield a white solid. 400 ml water was poured into the resulting solid and water was filtered off. The solid was washed with 400 ml water twice. To remove the trace amount of hydrazine, the white solid was taken up in 600 ml EtOAc and washed with 300 ml water twice and saturated brine solution. The EtOAc layer was then dried over sodium sulfate. Removal of the solvent gave the desired product as a white amorphous solid (60.0 g, yield=94%). The product was used directly for the next step without further purification.

3-Methyl-1H-indazole-5-carboxylic acid (4e): A three necked round bottom flask equipped with an internal thermometer and an overhead stir motor was charged with 600 mL of THF and chilled to −78° C. t-BuLi (1.7 M in THF, 200 mL, 0.340 mol) was added to the flask, and the mixture was stirred for 15 min. 5-Bromo-3-methyl-1H-indazole (4d) (22.4 g, 0.106 mol) in 200 mL THF was then added dropwise via an addition funnel. The rate of addition was closely monitored to insure that the internal temperature remained below −70° C. The resulting orange solution was stirred for 30 min, at which point $CO_2$ was bubbled through the mixture. A white precipitate was observed.

After 20 min, the ice bath was removed and the temperature allowed to warm to room temperatures (rt), and stir for an additional 30 min. Water was then added, 40 mL initially followed by a further 200 mL. The biphasic mixture was partially concentrated under reduced pressure, removing ~75% of the original organic portion. The biphasic solution was then transferred to an addition funnel, and the organic phase was extracted with 100 mL of 2M NaOH. The combined aqueous extracts were then washed with ether and then acidified to pH=2.0 with conc. HCl. A precipitate began to form and the mixture was cooled to 0° C. to complete the precipitation. The resulting solid was filtered, washed with 1 M HCl, and dried under reduced pressure at 160° C. over phosphorus pentoxide, affording 3-methyl-1H-indazole-5-carboxylic acid (4e) (18.1 g, 96% yield) as a pink/beige solid. $^1$H NMR 400 MHz (d$^4$ MeOH) 2.61 (3H, s), 3.33 (2H, s), 7.52 (1H, d, J=6.0 Hz), 8.05 (1H, t, J=5.2 Hz), 8.50 (1H, s). MS (API-ES) m/z (%): 177 (100%, M$^+$+H).

Two methods are used to prepare 5-(3-Methyl-1H-indazol-5-yl)-[1,3,4]thiadiazol-2-ylamine (4f). Method 1 uses a procedure similar to the preparation of 1a.

Method 2: To a round bottom flash equipped with an overhead stir motor was added 80 g of polyphosphoric acid. The flask was heated to 90° C. and a finely ground mixture of 3-methyl-1H-indazole-5-carboxylic acid 4e (8.0 g, 45.5 mmol) and thiosemicarbazide (4.1 g (45.4 mmol) was slowly added over a period of 30 min. The resulting mixture was stirred for 24 hr. At this point 200 ml of ice water was added to the solution, and the pH of the resulting mixture was adjusted to 7.0 using solid KOH. A precipitate was formed in the process. The precipitate was isolated by filtration, washed sequentially with water and ether, and dried at reduced pressure, affording 5-(3-Methyl-1H-indazol-5-yl)-[1,3,4]thiadiazol-2-ylamine (4f) (5.50 g, 53% yield) as a tan colored solid. $^1$H 400 MHz NMR (d$^6$ DMSO), 2.54 (3H, s), 3.17 (1H, s), 7.54 (1H, d, J=8.0 Hz), 7.83 (1H, t, J=8.0 Hz), 8.06 (1H, s). MS (API-ES) m/z (%): 232 (100%, M$^+$+H).

5-(5-Bromo-[1,3,4]thiadiazol-2-yl)-3-methyl-1H-indazole (4g): A suspension of 5-(3-Methyl-1H-indazol-5-yl)-[1,3,4]thiadiazol-2-ylamine (4f) (1.10 g, 4.76 mmol) in 20 ml acetonitrile was added into a mixture of tert-butyl nitrite (0.74 g, 7.14 mmol) and copper(IT) bromide (1.27 g, 5.71 mmol) that was preheated to 60° C. The resulting mixture was heated at 60° C. for 2 hours. After removing all the solvent via evaporation under reduce pressure, the remaining residue was partitioned between ethylacetate and saturated brine. The ethylacetate solution was washed with brine and dried over sodium sulfate. An orange solid was obtained after removing the solvent as the crude product (1.10 g). It was used directly for next step. MS (API-ES) m/z (%): 295 (100%, M$^+$+1), 297 (97%, M$^+$+3).

Example 4

S—N-[5-(3-Methyl-1H-indazol-5-yl)-[1,3,4]thiadiazol-2-yl]-3-phenyl-propane-1,2-diamine (4): Example 4 was synthesized in a way similar to example 1 using 4g and S-3-phenyl-propane-1,2-diamine as the starting materials. It was purified by a reverse phase HPLC procedure as a TFA salt: $^1$H NMR (400 MHz, Methanol-d$_4$): δ 2.60 (s, 3H), 3.06 (m, 2H), 3.64 (m, 1H), 3.74 (m, 1H), 3.88 (m, 1H), 7.35 (m, 5H), 7.57 (d, J=8.8 Hz, 1H), 7.87 (d, J=8.8 Hz, 1H), 8.08 (s, 1H); MS (API-ES) m/z (%): 365 (100%, M$^+$+1), 751 (60%, 2M+Na$^+$); HRMS (ESI): calculated for $C_{19}H_{21}N_6S$ [M+1]: 365.1543; found: 365.1542.

Example 5

S-3-(1H-Indol-3-yl)-N-[5-(3-methyl-1H-indazol-5-yl)-[1,3,4]thiadiazol-2-yl]-propane-1,2-diamine (5): Example 5 was synthesized in a way similar to example 1 using 4g and S-3-(1H-Indol-3-yl)-propane-1,2-diamine as the starting materials. It was purified by a reverse phase HPLC procedure as a TFA salt: $^1$H NMR (400 MHz, Methanol-d$_4$): δ 2.62 (s, 3H), 3.18 (m, 1H), 3.25 (m, 1H), 3.67 (m, 1H), 3.79 (m, 1H), 3.99 (m, 1H), 7.09 (t, J=7.2 Hz, 1H), 7.17 (t, J=7.2 Hz, 1H), 7.29 (s, 1H), 7.42 (d, J=8.4 Hz, 1H), 7.58 (d, J=8.8 Hz, 1H), 7.63 (d, J=7.6 Hz, 1H), 7.89 (dd, J=8.4, 1.2 Hz, 1H), 8.10 (s, 1H); MS (API-ES) m/z (%): 404 (100%, M$^+$+1), 829 (30%, 2M+Na$^+$); HRMS (ESI): calculated for $C_{21}H_{22}N_7S$ [M+H]: 404.1652; found: 404.1651.

Examples 6-69 were synthesized using the following general procedure as shown in Scheme 4:

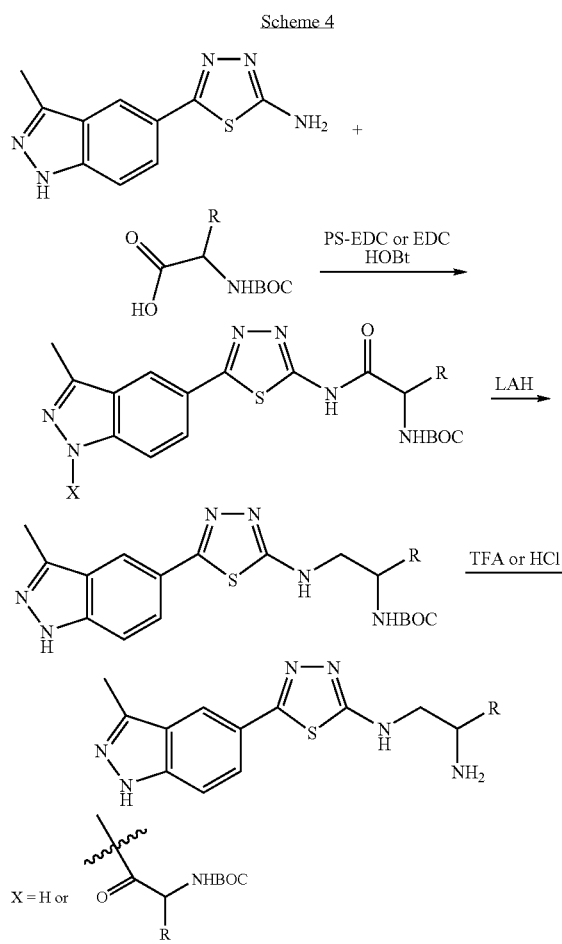

General procedure for the aminothiadiazole amide bond formation reaction: 150 mg aminothiadiazole (0.65 mmol, 1 equiv.) was dissolved in 6 ml DMF and PS-EDC (1083 mg, 1.95 mmol, 3 equiv.), HOBt (263 mg, 1.95 mmol, 3 equiv.) and the corresponding acid (1.95 mmol, 3 equiv.) were added. The reaction mixture was stirred overnight at room temperature and filtered. The resin was washed 3 times with 20 ml DMF (each) and the combined DMF phases were evaporated. The crude yellow oil was subjected to the next reduction step without further purification.

General procedure for the lithium aluminum hydride (LAH) induced amide reduction: The crude product from the previous step was dissolved in 5 ml of THF and cooled to 0° C. 6 ml of LAH was added (1M in THF) and the cooling bath was removed. Stirring was continued for 2 h at room temperature. 50 ml of dry THF was added and the reaction mixture was poured into a stirring mixture of 10 g $Na_2SO_4 \cdot 10 \times H_2O$ in 50 ml of THF. Stirring was continued at room temperature for 30 min and the reaction mixture was filtered. After washing (3 times with 80 ml $CH_2Cl_2$ each) and drying of the combined organic layers over $MgSO_4$, the mixture was evaporated. The crude product was partially purified on 2 preparative TLCs, leading to the reduced intermediate with an average purity between 75-85%. This material was used without further purification in the final BOC-deprotection step.

General procedure for the TFA induced BOC deprotection: The semi-pure material from the previous reaction was dissolved in 10 ml $CH_2Cl_2$ and 3 ml of TFA was added at room temp. The reaction was stirred at room temperature for 2 h and 50 ml of toluene were added. The reaction mixture was evaporated and redissolved in 2 ml of methanol. The pH of the mixture was increased with 5M $NaOH_{(aq)}$ (3-10 drops from a Pasteur pipette) and loaded onto a preparative TLC plate for purification purposes (10% MeOH in $CH_2Cl_2$) leading to the free amines. To obtain the corresponding HCl salts of the compounds, the preparative TLC silica gel washing solutions were acidified with 1 ml of HCl (1M in $Et_2O$) prior to evaporation. The corresponding TFA salts were obtained in case an additional purification step on a preparative HPLC (TFA buffer) was required.

Example 6

2-[5-(3-Methyl-1H-indazol-5-yl)-[1,3,4]thiadiazol-2-ylamino]-1-(tetrahydro-pyran-4-ylmethyl)-ethyl-ammonium trifluoro-acetate (6). MS (API-ES) m/z (%): 373 (100%, $M^++1$), 374 (25%, $M^++2$), 395 (10%, $M^++23$), 767 (33%, $2M^++23$).

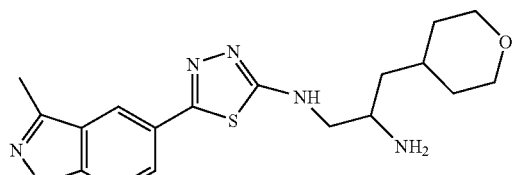

Example 7

(S)-{1-Benzyl-2-[5-(3-methyl-1H-indazol-5-yl)-[1,3,4]thiadiazol-2-ylamino]-ethyl}-methyl-ammonium trifluoro-acetate (7). MS (API-ES) m/z (%): 379 (100%, $M^++1$), 380 (25%, $M^++2$), 401 (10%, $M^++23$), 779 (25%, $2M^++23$).

Example 8

(R)-1-[5-(3-Methyl-1H-indazol-5-yl)-[1,3,4]thiadiazol-2-ylcarbamoyl]-2-phenyl-ethyl-ammonium chloride (8). MS (API-ES) m/z (%): 365 (100%, $M^++1$), 366 (25%, $M^++2$), 387 (33%, $M^++23$), 751 (85%, $2M^++23$).

Example 9

(2-Methylamino-1,2,3,4-tetrahydro-naphthalen-2-ylmethyl)-[5-(3-methyl-1H-indazol-5-yl)-[1,3,4]thiadiazol-2-yl]-amine (9). MS (API-ES) m/z (%): 405 (100%, $M^++1$), 427 (15%, $M^++23$), 831 (75%, $2M^++23$).

Example 10

(2-Methylamino-indan-2-ylmethyl)-[5-(3-methyl-1H-indazol-5-yl)-[1,3,4]thiadiazol-2-yl]-amine (10). MS (API-ES) m/z (%): 391 (100%, $M^++1$), 413 (10%, $M^++23$), 803 (75%, $2M^++23$).

Example 11

(S)-[5-(3-Methyl-1H-indazol-5-yl)-[1,3,4]thiadiazol-2-yl]-(2-methyl-1,2,3,4-tetrahydro-isoquinolin-3-ylmethyl)-amine (11). MS (API-ES) m/z (%): 391 (100%, $M^++1$), 413 (7%, $M^++23$), 803 (15%, $2M^++23$).

Example 12

N²-[5-(3-Methyl-1H-indazol-5-yl)-[1,3,4]thiadiazol-2-yl]-1-(1,2,3,4-tetrahydro-naphthalen-2-yl)-ethane-1,2-diamine (12). MS (API-ES) m/z (%): 405 (100%, M⁺+1), 427 (30%, M⁺+23), 831 (95%, 2M⁺+23).

Example 13

(2-Amino-indan-2-ylmethyl)-[5-(3-methyl-1H-indazol-5-yl)-[1,3,4]thiadiazol-2-yl]-amine (13). MS (API-ES) m/z (%): 377 (85%, M⁺+1), 399 (15%, M⁺+23), 775.2 (100%, 2M⁺+23).

Example 14

(2-Amino-1,2,3,4-tetrahydro-naphthalen-2-ylmethyl)-[5-(3-methyl-1H-indazol-5-yl)-[1,3,4]thiadiazol-2-yl]-amine (14). MS (API-ES) m/z (%): 391 (100%, M⁺+1), 413 (10%, M⁺+23), 803 (20% 2M⁺+23).

Example 15

(S)-3-(3-Fluoro-phenyl)-N-[5-(3-methyl-1H-indazol-5-yl)-[1,3,4]thiadiazol-2-yl]-propane-1,2-diamine (15). MS (API-ES) m/z (%): 383 (100%, M⁺+1), 405 (8%, M⁺+23), 787 (55%, 2M⁺+23).

Example 16

(S)-3-(3,4-Difluoro-phenyl)-N-[5-(3-methyl-1H-indazol-5-yl)-[1,3,4]thiadiazol-2-yl]-propane-1,2-diamine (16). MS (API-ES) m/z (%): 401 (100%, M⁺+1), 423 (8%, M⁺+23), 823 (65%, 2M⁺+23).

Example 17

(S)—N¹-[5-(3-Methyl-1H-indazol-5-yl)-[1,3,4]thiadiazol-2-yl]-3-pyridin-2-yl-propane-1,2-diamine (17). MS (API-ES) m/z (%): 366 (100%, M⁺+1), 388 (35%, M⁺+23), 753 (40%, 2M⁺+23).

Example 18

(S)-3-(3,4-Dichloro-phenyl)-N-[5-(3-methyl-1H-indazol-5-yl)-[1,3,4]thiadiazol-2-yl]-propane-1,2-diamine (18). MS (API-ES) m/z (%): 433 (100%, M⁺+1), 435 (65%, M⁺+3), 887 (15%, 2M⁺+23), 889 (20% 2M⁺+25).

Example 19

(S)-1-(1H-Indol-2-ylmethyl)-3-[5-(3-methyl-1H-indazol-5-yl)-[1,3,4]thiadiazol-2-ylamino]-propyl-ammonium trifluoro-acetate (19). MS (API-ES) m/z (%): 418 (100%, M⁺+1), 440 (30%, M⁺+23), 857 (50%, 2M⁺+23).

Example 20

(2-Hydroxy-3-phenyl-propyl)-[5-(3-methyl-1H-indazol-5-yl)-[1,3,4]thiadiazol-2-yl]-ammonium trifluoro-acetate (20). MS (API-ES) m/z (%): 366 (100%, M⁺+1), 388 (20%, M⁺+23).

Example 21

(2-Hydroxy-3-phenoxy-propyl)-[5-(3-methyl-1H-indazol-5-yl)-[1,3,4]thiadiazol-2-yl]-ammonium trifluoro-acetate (21). MS (API-ES) m/z (%): 382 (100%, M⁺+1), 404 (18%, M⁺+23).

Example 22

(1S,2S)-1-{[5-(3-Methyl-1H-indazol-5-yl)-[1,3,4]thiadiazol-2-ylamino]-methyl}-2-phenyl-propyl-ammonium chloride (22). MS (API-ES) m/z (%): 379 (100%, M⁺+1), 401 (40%, M⁺+23), 779 (80%, 2M⁺+23).

Example 23

(S)-2-[5-(3-Methyl-1H-indazol-5-yl)-[1,3,4]thiadiazol-2-ylamino]-1-(4-trifluoromethyl-benzyl)-ethyl-ammonium chloride (23). MS (API-ES) m/z (%): 433 (100%, M⁺+1), 455 (20%, M⁺+23), 887 (55%, 2M⁺+23).

Example 24

(S)-2-(2-Bromo-phenyl)-1-{[5-(3-methyl-1H-indazol-5-yl)-[1,3,4]thiadiazol-2-ylamino]-methyl}-ethyl-ammonium trifluoro-acetate (24). MS (API-ES) m/z (%): 443 (95%, M⁺+1), 445 (100%, M⁺+3).

Example 25

(S)-2-(4-Ethyl-phenyl)-1-{[5-(3-methyl-1H-indazol-5-yl)-[1,3,4]thiadiazol-2-ylamino]-methyl}-ethyl-ammonium trifluoro-acetate (25). MS (API-ES) m/z (%): 393 (100%, M⁺+1), 415 (15%, M⁺+23), 807 (45%, 2M⁺+23).

Example 26

(S)-1-(3,5-Difluoro-benzyl)-2-[5-(3-methyl-1H-indazol-5-yl)-[1,3,4]thiadiazol-2-ylamino]-ethyl-ammonium chloride (26). MS (API-ES) m/z (%): 401 (100%, M⁺+1), 423 (15%, M⁺+23), 823 (75%, 2M⁺+23).

Example 27

(S)-1-(2-Methoxy-benzyl)-2-[5-(3-methyl-1H-indazol-5-yl)-[1,3,4]thiadiazol-2-ylamino]-ethyl-ammonium chloride (27). MS (API-ES) m/z (%): 395 (100%, M⁺+1), 417 (25%, M⁺+23), 811 (50%, 2M⁺+23).

Example 28

(S)-1-{[5-(3-Methyl-1H-indazol-5-yl)-[1,3,4]thiadiazol-2-ylamino]-methyl}-2-(2-pyrimidin-2-yl-phenyl)-ethyl-ammonium trifluoro-acetate (28). MS (API-ES) m/z (%): 443 (100%, M⁺+1), 465 (15%, M⁺+23).

Example 29

(S)-1-(3,4-Dimethoxy-benzyl)-2-[5-(3-methyl-1H-indazol-5-yl)-[1,3,4]thiadiazol-2-ylamino]-ethyl-ammonium chloride (29). MS (API-ES) m/z (%): 425 (100%, M⁺+1), 849 (10%, 2M⁺+1), 871 (8%, 2M⁺+23).

Example 30

(S)-2-[5-(3-Methyl-1H-indazol-5-yl)-[1,3,4]thiadiazol-2-ylamino]-1-phenyl-ethyl-ammonium chloride (30). MS (API-ES) m/z (%): 351 (100%, M$^+$+1), 373 (5%, M$^+$+23), 723 (25%, 2M$^+$+23).

Example 31

(S)-3-(4-Methoxy-phenyl)-N-[5-(3-methyl-1H-indazol-5-yl)-[1,3,4]thiadiazol-2-yl]-propane-1,2-diamine (31). HRMS (ESI): calcd. for $C_{20}H_{23}N_6OS$ [M$^+$+H], 395.16486; found 395.16511.

Example 32

(S)—N-[5-(3-Methyl-1H-indazol-5-yl)-[1,3,4]thiadiazol-2-yl]-4-phenyl-butane-1,2-diamine (32). HRMS (ESI): calcd for $C_{20}H_{23}N_6S$ [M$^+$+H], 379.17041; found: 379.16994.

Example 33

(S)-[5-(3-Methyl-1H-indazol-5-yl)-[1,3,4]thiadiazol-2-yl]-(2,3,4,9-tetrahydro-1H-β-carbolin-3-ylmethyl)-amine (33). HRMS (ESI): calcd for $C22H_{22}N_7S$ [M$^+$+H], 416.16519, found: 416.16537.

Example 34

(S)-3-(2-Fluoro-phenyl)-N-[5-(3-methyl-1H-indazol-5-yl)-[1,3,4]thiadiazol-2-yl]-propane-1,2-diamine (34). HRMS (ESI): calcd for $C_{19}H_{20}FN_6S$ [M$^+$+H], 383.14487; found 383.14511.

Example 35

(S)-3-(2-Chloro-phenyl)-N-[5-(3-methyl-1H-indazol-5-yl)-[1,3,4]thiadiazol-2-yl]-propane-1,2-diamine (35). HRMS (ESI): calcd for $C_{19}H_2ClN_6S$[M$^+$+H], 399.11532; found 399.11554.

Example 36

(S)—N-[5-(3-Methyl-1H-indazol-5-yl)-[1,3,4]thiadiazol-2-yl]-3-o-tolyl-propane-1,2-diamine (36). HRMS (ESI): calcd for $C_{20}H_{23}N_6S$ [M$^+$+H], 379.16994; found 379.17011.

Example 37

(S)—N-[5-(3-Methyl-1H-indazol-5-yl)-[1,3,4]thiadiazol-2-yl]-3-(3-trifluoromethyl-phenyl)-propane-1,2-diamine (37). HRMS (ESI): calcd for $C_{20}H_{20}F_3N_6S$ [M$^+$+H], 433.14168; found 433.14208.

Example 38

(R)-3-(2-Chloro-phenyl)-N-[5-(3-methyl-1H-indazol-5-yl)-[1,3,4]thiadiazol-2-yl]-propane-1,2-diamine (38). HRMS (ESI): calcd for $C_{19}H_2ClN_6S$ [M$^+$+H], 399.11532; found 399.11575.

Example 39

(S)-3-(4-Fluoro-phenyl)-N-[5-(3-methyl-1H-indazol-5-yl)-[1,3,4]thiadiazol-2-yl]-propane-1,2-diamine (39). HRMS (ESI): calcd for $C_{19}H_{20}FN_6S$ [M$^+$+H], 383.14487; found 383.14465.

Example 40

(S)—N-[5-(3-Methyl-1H-indazol-5-yl)-[1,3,4]thiadiazol-2-yl]-3-pyridin-3-yl-propane-1,2-diamine (40). HRMS (ESI): calcd for $C_{18}H_{20}N_7S$ [M$^+$+H], 366.14954 found 366.14995.

Example 41

(S)—N-[5-(3-Methyl-1H-indazol-5-yl)-[1,3,4]thiadiazol-2-yl]-3,3-diphenyl-propane-1,2-diamine (41). HRMS (ESI): calcd for $C_{25}H_{25}N_6S$ [M$^+$+H], 441.18559; found 441.18616.

Example 42

(S)-3-(4-Chloro-phenyl)-N-[5-(3-methyl-1H-indazol-5-yl)-[1,3,4]thiadiazol-2-yl]-propane-1,2-diamine (42). HRMS (ESI): calcd for $C_{19}H_{20}ClN_6S$ [M$^+$+H], 399.11532; found 399.11578.

Example 43

(S)—N-[5-(3-Methyl-1H-indazol-5-yl)-[1,3,4]thiadiazol-2-yl]-3-m-tolyl-propane-1,2-diamine (43). FTMS Theoretical (M+H) 379.16994, found 379.16979.

Example 44

(S)—N-[5-(3-Methyl-1H-indazol-5-yl)-[1,3,4]thiadiazol-2-yl]-3-thiophen-2-yl-propane-1,2-diamine (44). FTMS Theoretical (M+H) 371.11071, found 371.11044.

Example 45

(S)—N-[5-(3-Methyl-1H-indazol-5-yl)-[1,3,4]thiadiazol-2-yl]-3-(2-trifluoromethyl-phenyl)-propane-1,2-diamine (45). FTMS Theoretical (M+H) 433.14168, found 433.14131.

Example 46

5-(3-methyl-1H-indazol-5-yl)-N-(((2S,3R)-3-phenylpyrrolidin-2-yl)methyl)-1,3,4-thiadiazol-2-amine (46). FTMS Theoretical (M+H) 391.16994, found 391.17039.

Example 47

(S)-3-(3-Methoxy-phenyl)-N1-[5-(3-methyl-1H-indazol-5-yl)-[1,3,4]thiadiazol-2-yl]-propane-1,2-diamine (47). FTMS Theoretical (M+H) 395.16486, found 395.16545.

Example 48

5-(3-methyl-1H-indazol-5-yl)-N-(((2S,4S)-4-phenylpyrrolidin-2-yl)methyl)-1,3,4-thiadiazol-2-amine (48). FTMS Theoretical (M+H) 391.16994, found 391.17009.

Example 49

N—((S)-2-amino-2-(2,3-dihydro-1H-inden-2-yl)ethyl)-5-(3-methyl-1H-indazol-5-yl)-1,3,4-thiadiazol-2-amine (49). FTMS Theoretical (M+H) 391.16994, found 391.17051.

Example 50

(2S)-4-(5-(3-methyl-1H-indazol-5-yl)-1,3,4-thiadiazol-2-ylamino)-1-phenylbutan-2-aminium 2,2,2-trifluoroacetate (50). MS (API-ES) m/z (%): 379.2 (100%, M++1), 380.1 (25%, M++2), 381.3 (10%, M++3).

Example 51

N—((S)-2-amino-3-(4-ethoxyphenyl)propyl)-5-(3-methyl-1H-indazol-5-yl)-1,3,4-thiadiazol-2-amine (51). LCMS (M+H) 409.2 calc. for C21H25N6OS 409.18.

Example 52

N—((S)-2-amino-3-(1H-imidazol-5-yl)propyl)-5-(3-methyl-1H-indazol-5-yl)-1,3,4-thiadiazol-2-amine (52). MS (API-ES) m/z (%): 355 (100%, M++H).

Example 53

N—((S)-2-amino-3-(3-bromophenyl)propyl)-5-(3-methyl-1H-indazol-5-yl)-1,3,4-thiadiazol-2-amine (53). MS (API-ES) m/z (%): 444 (100%, M++H).

Example 54

N—((S)-2-amino-4-(4-methoxyphenyl)butyl)-5-(3-methyl-1H-indazol-5-yl)-1,3,4-thiadiazol-2-amine (54). MS (API-ES) m/z (%): 409 (100%, M++H).

| Ex. No. | Structure | Name | Molecular Formula | Theoretical (M + H) | Measured (M + H) FTMS |
|---|---|---|---|---|---|
| 55 | 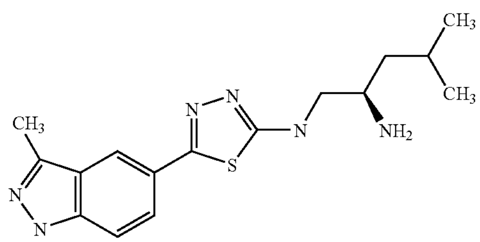 | N-((R)-2-amino-3-(4-tert-butylphenyl)propyl)-5-(1H-indazol-5-yl)-1,3,4-thiadiazol-2-amine | C$_{16}$H$_{22}$N$_6$S | 331.16990 | 331.17024 |
| 56 | 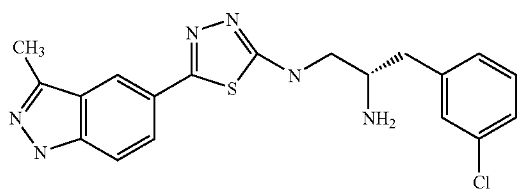 | N-((S)-2-amino-3-(3-chlorophenyl)propyl)-5-(3-methyl-1H-indazol-5-yl)-1,3,4-thiadiazol-2-amine | C$_{19}$H$_{19}$ClN$_6$S | 399.11532 | 399.11569 |
| 57 | 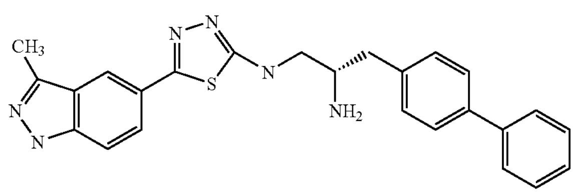 | N-((S)-2-amino-3-((4-phenyl)phenyl)propyl)-5-(3-methyl-1H-indazol-5-yl)-1,3,4-thiadiazol-2-amine | C$_{25}$H$_{24}$N$_6$S | 441.18559 | 441.18568 |
| 58 | 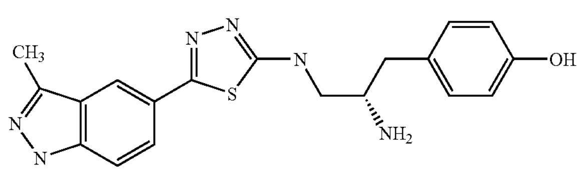 | 4-((S)-2-amino-3-(5-(3-methyl-1H-indazol-5-yl)-1,3,4-thiadiazol-2-ylamino)propyl)phenol | C$_{19}$H$_{20}$N$_6$OS | 381.14921 | 381.14943 |
| 59 | 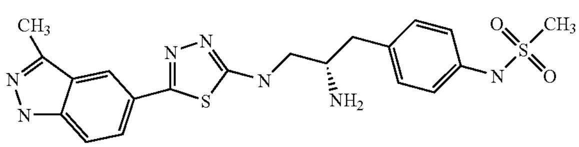 | N-(4-((S)-2-amino-3-(5-(3-methyl-1H-indazol-5-yl)-1,3,4-thiadiazol-2-ylamino)propyl)phenyl)methanesulfonamide | C$_{20}$H$_{23}$N$_7$O$_2$S$_2$ | 458.14274 | 458.14300 |
| 60 | 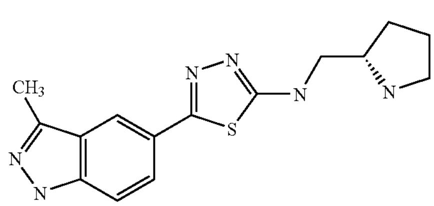 | 5-(3-methyl-1H-indazol-5-yl)-N-((S)-pyrrolidin-2-ylmethyl)-1,3,4-thiadiazol-2-amine | C$_{15}$H$_{18}$N$_6$S | 315.13864 | 315.13863 |

| Ex. No. | Structure | Name | Molecular Formula | Theoretical (M + H) | Measured (M + H) FTMS |
|---|---|---|---|---|---|
| 61 | 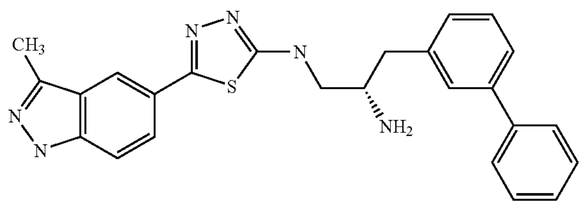 | N-((S)-2-amino-3-((3-phenyl)phenyl)propyl)-5-(3-methyl-1H-indazol-5-yl)-1,3,4-thiadiazol-2-amine | $C_{25}H_{24}N_6S$ | 441.18559 | 441.18513 |
| 62 | 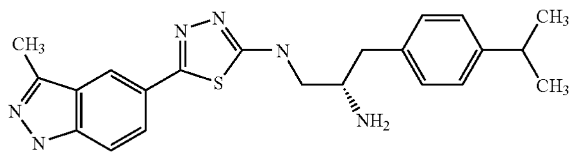 | N-((S)-2-amino-3-(4-isopropylphenyl)propyl)-5-(3-methyl-1H-indazol-5-yl)-1,3,4-thiadiazol-2-amine | $C_{22}H_{26}N_6S$ | 407.20124 | 407.20095 |
| 63 | 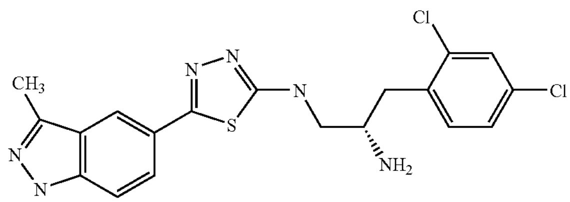 | N-((S)-2-amino-3-(2,4-dichlorophenyl)propyl)-5-(3-methyl-1H-indazol-5-yl)-1,3,4-thiadiazol-2-amine | $C_{19}H_{18}Cl_2N_6S$ | 433.07635 | 433.07657 |
| 64 | 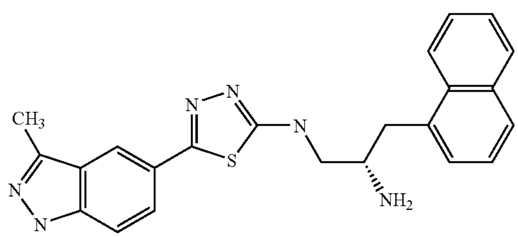 | N-((S)-2-amino-3-(naphthalen-1-yl)propyl-5-(3-methyl-1H-indazol-5-yl)-1,3,4-thiadiazol-2-amine | $C_{23}H_{22}N_6S$ | 415.16994 | 415.16976 |
| 65 | 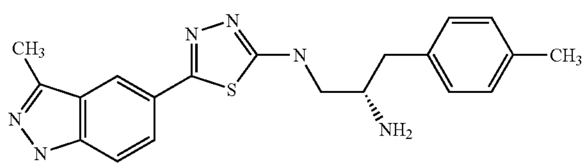 | N-((S)-2-amino-3-ptolylpropyl)-5-(3-methyl-1H-indazol-5-yl)-1,3,4-thiadiazol-2-amine | $C_{20}H_{22}N_6S$ | 379.16994 | 379.17001 |
| 66 | 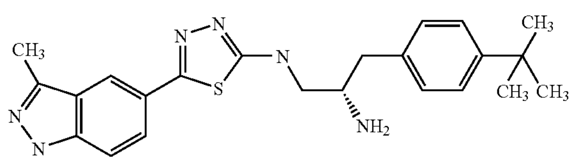 | N-((S)-2-amino-3-(4-tert-butylphenyl)propyl)-5-(3-methyl-1H-indazol-5-yl)-1,3,4-thiadiazol-2-amine | $C_{23}H_{28}N_6S$ | 421.21689 | 421.21648 |
| 67 | 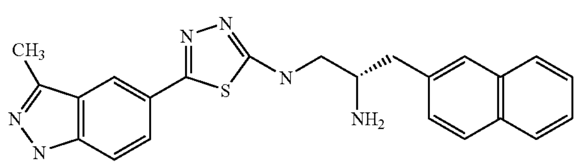 | N-((S)-2-amino-3-(naphthalen-2-yl)propyl-5-(3-methyl-1H-indazol-5-yl)-1,3,4-thiadiazol-2-amine | $C_{23}H_{22}N_6S$ | 415.16994 | 415.17026 |
| 68 | 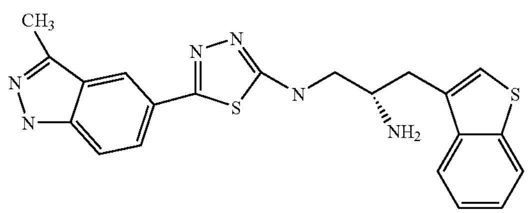 | N-((S)-2-amino-3-(benzo[b]thiophen-3-yl)propyl)-5-(3-methyl-1H-indazol-5-yl)-1,3,4-thiadiazol-2-amine | $C_{21}H_{20}N_6S_2$ | 421.12636 | 421.12660 |

Example 69

5-(1H-indazol-5-yl)-1,3,4-thiadiazol-2-amine was synthesized in a way similar to that of 4f as shown in Scheme 3 with commercially available 5-bromo-2-fluorobenzaldehyde as the starting material in three steps. MS (API-ES) m/z (%): 218 (100%, M$^+$+1).

Examples 70-87 were synthesized in a manner similar to that as shown in Scheme 4 using Example 69 (5-(1H-indazol-5-yl)-1,3,4-thiadiazol-2-amine) as the starting material.

| Ex. No. | Structure | Name | Molecular Formula | Theoretical (M + H) | Measured (M + H) |
|---|---|---|---|---|---|
| 70 | 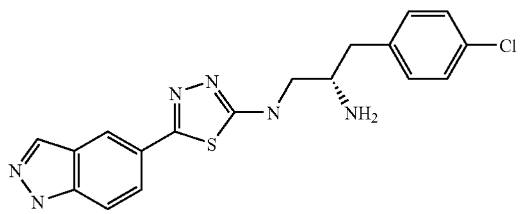 | N-((S)-2-amino-3-(4-chlorophenyl)propyl)-5-(1H-indazol-5-yl)-1,3,4-thiadiazol-2-amine | $C_{18}H_{17}ClN_6S$ | 385.09967 | 385.09996 |
| 71 | 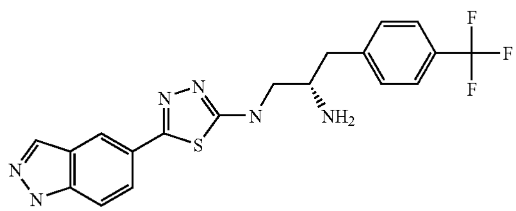 | N-((S)-2-amino-3-(4-(trifluoromethyl)phenyl)propyl)-5-(1H-indazol-5-yl)-1,3,4-thiadiazol-2-amine | $C_{19}H_{17}F_3N_6S$ | 419.12603 | 419.12604 |
| 72 | 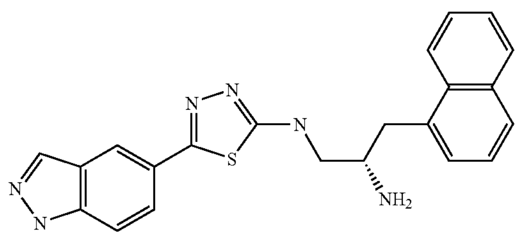 | N-((S)-2-amino-3-(naphthalen-1-yl)propyl)-5-(1H-indazol-5-yl)-1,3,4-thiadiazol-2-amine | $C_{22}H_{20}N_6S$ | 401.15429 | 401.15391 |
| 73 | 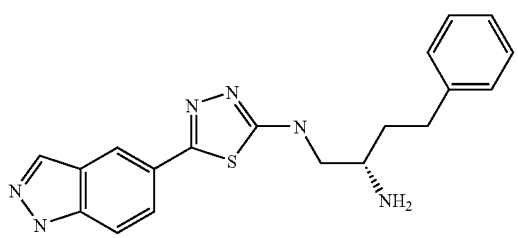 | N-((S)-2-amino-4-phenylbutyl)-5-(1H-indazol-5-yl)-1,3,4-thiadiazol-2-amine | $C_{19}H_{20}N_6S$ | 365.14702 | 365 MS (API-ES) |
| 74 | 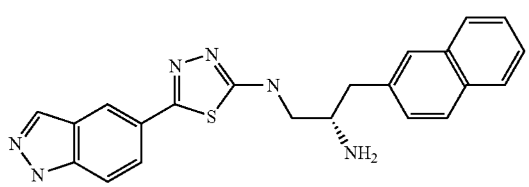 | N-((S)-2-amino-3-(naphthalen-2-yl)propyl)-5-(1H-indazol-5-yl)-1,3,4-thiadiazol-2-amine | $C_{22}H_{20}N_6S$ | 400.14702 | 401 MS (API-ES) |
| 75 | 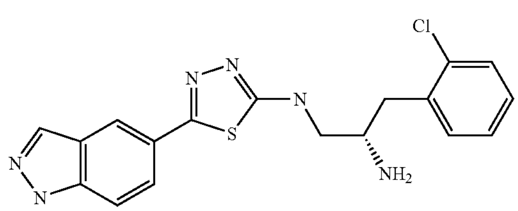 | N-((S)-2-amino-3-(2-chlorophenyl)propyl)-5-(1H-indazol-5-yl)-1,3,4-thiadiazol-2-amine | $C_{18}H_{17}ClN_6S$ | 385.09967 | 385.09932 |

-continued

| Ex. No. | Structure | Name | Molecular Formula | Theoretical (M + H) | Measured (M + H) |
|---|---|---|---|---|---|
| 76 | 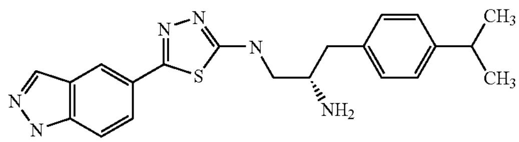 | N-((S)-2-amino-3-(4-isopropylphenyl)propyl)-5-(1H-indazol-5-yl)-1,3,4-thiadiazol-2-amine | $C_{21}H_{24}N_6S$ | 393.18559 | 393.18528 |
| 77 | 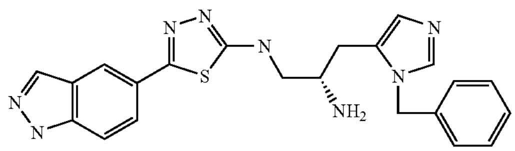 | N-((S)-2-amino-3-(1-benzyl-1H-indazol-5-yl)propyl-5-indazol-5-yl)-1,3,4-thiadiazol-2-amine | $C_{22}H_{22}N_8S$ | 431.176909 | 431.17653 |
| 78 | 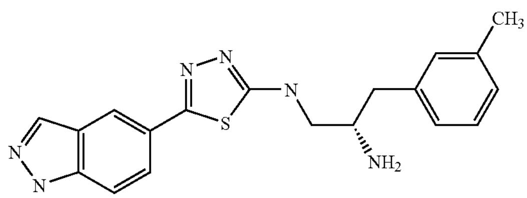 | N-((S)-2-amino-3-m-tolylpropyl)-5-(1H-indazol-5-yl)-1,3,4-thiadiazol-2-amine | $C_{19}H_{20}N_6S$ | 365.15429 | 365.15435 |
| 79 | 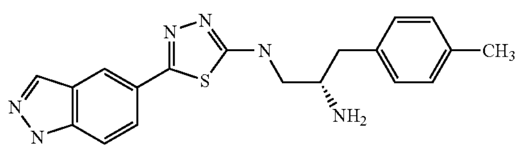 | N-((S)-2-amino-3-p-tolylpropyl)-5-(1H-indazol-5-yl)-1,3,4-thiadiazol-2-amine | $C_{19}H_{20}N_6S$ | 365.154.29 | 365.15458 |
| 80 | 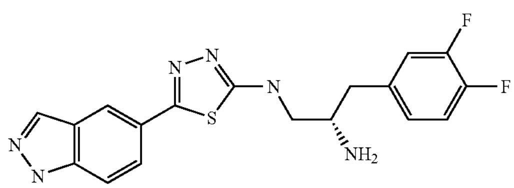 | N-((S)-2-amino-3-(3,4-difluorophenyl)propyl)-5-(1H-indazol-5-yl)-1,3,4-thiadiazol-2-amine | $C_{18}H_{16}F_2N_6S$ | 387.11980 | 387.11959 |
| 81 | 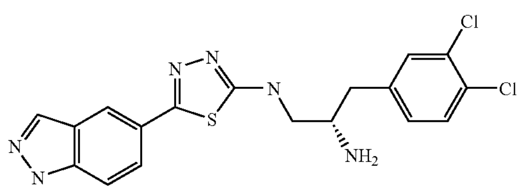 | N-((S)-2-amino-3-(3,4-dichlorophenyl)propyl)-5-(1H-indazol-5-yl)-1,3,4-thiadiazol-2-amine | $C_{18}H_{16}Cl_2N_6S$ | 419.06070 | 419.06058 |
| 82 | 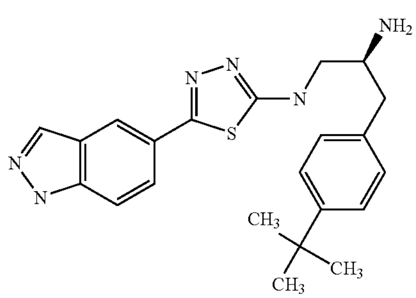 | N-((S)-2-amino-3-(4-tert-butylphenyl)propyl)-5-(1H-indazol-5-yl)-1,3,4-thiadiazol-2-amine | $C_{22}H_{26}N_6S$ | 407.20124 | 407.20120 |
| 83 | 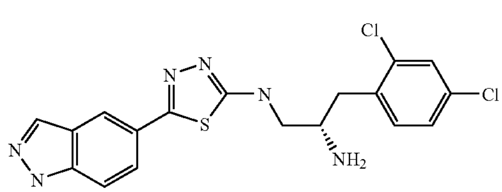 | N-((S)-2-amino-3-(2,4-dichlorophenyl)propyl)-5-(1H-indazol-5-yl)-1,3,4-thiadiazol-2-amine | $C_{18}H_{16}Cl_2N_6S$ | 419.06070 | 419.06111 |

-continued

| Ex. No. | Structure | Name | Molecular Formula | Theoretical (M + H) | Measured (M + H) |
|---|---|---|---|---|---|
| 84 | 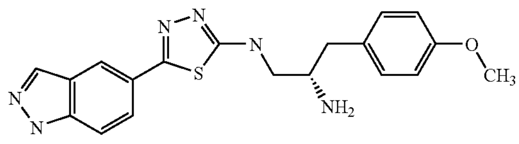 | N-((S)-2-amino-3-(4-methoxyphenyl)propyl)-5-(1H-indazol-5-yl)-1,3,4-thiadiazol-2-amine | $C_{19}H_{20}N_6OS$ | 381.14921 | 381.14908 |
| 85 | 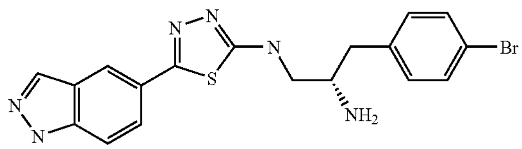 | N-((S)-2-amino-3-(4-bromophenyl)propyl)-5-(1H-indazol-5-yl)-1,3,4-thiadiazol-2-amine | $C_{18}H_{17}BrN_6S$ | 429.04915 | 429.04956 |
| 86 | 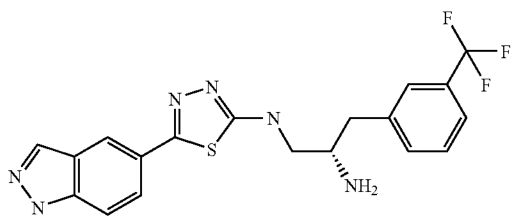 | N-((S)-2-amino-3-(3-(trifluoromethyl)phenyl)propyl)-5-(1H-indazol-5-yl)-1,3,4-thiadiazol-2-amine | $C_{19}H_{17}F_3N_6S$ | 419.12603 | 419.12659 |
| 87 | 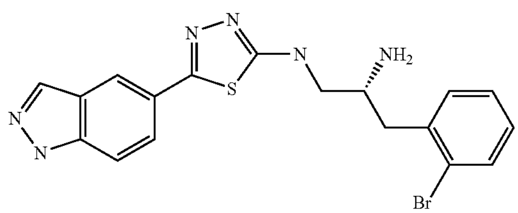 | N-((R)-2-amino-3-(2-bromophenyl)propyl)-5-(1H-indazol-5-yl)-1,3,4-thiadiazol-2-amine | $C_{18}H_{17}BrN_6S$ | 429.04915 | 429.04952 |

Example 88

5-(6-fluoro-1H-indazol-5-yl)-1,3,4-thiadiazol-2-amine (88):

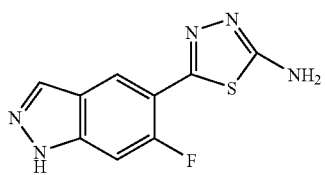

This compound was prepared in a manner similar to that shown in Scheme 3, using 5-bromo-6-fluoro-1H-indazole (88d), which was treated with t-butyl lithium and carbon dioxide to yield 6-fluoro-1H-indazole-5-carboxylic acid. This compound in turn was treated with thiosemicarbazide and polyphosphoric acid to form 5-(6-fluoro-1H-indazol-5-yl)-1,3,4-thiadiazol-2-amine. MS (API-ES) m/z (%): 236 (100%, M$^+$+1).

The procedures for making the intermediates of Example 88 are shown below in Scheme 5.

Scheme 5

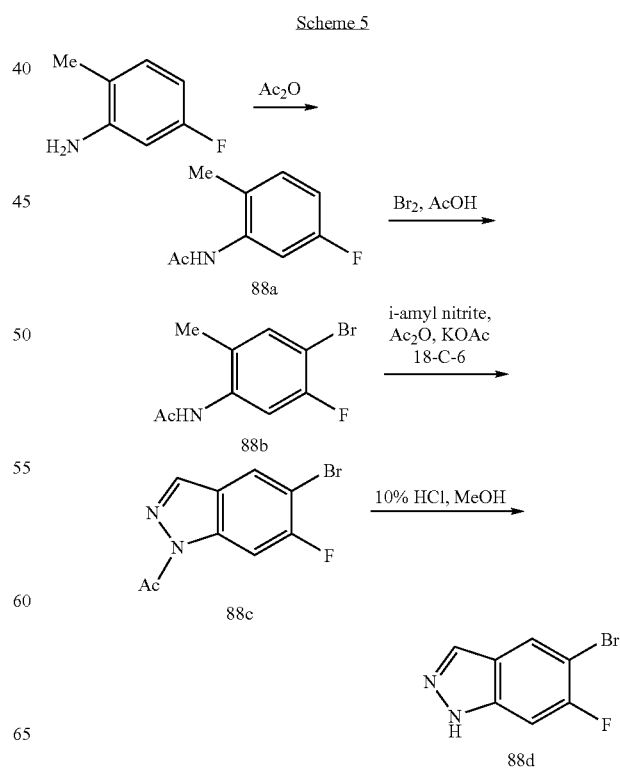

The starting material, 5-fluoro-2-methylbenzenamine (12.37 g, 99 mmol), was dissolved in toluene (120 mL) and acetic anhydride was added (12.5 mL, 113 mmol). The mixture was heated to 100° C. for 1 h. All solvents were removed in vacuo, and the resulting solid (88a) was dissolved in acetic acid (70 mL) and then bromine (4.82 mL, 94 mmol) was added dropwise. The dark solution was allowed to stir at room temperature for 12 h, during which time a tan precipitate formed.

The precipitate was crushed and taken up in water (50 mL), filtered, and washed with water (50 mL) to give N-(4-bromo-5-fluoro-2-methylphenyl)acetamide (88b) in 94% yield. The heated at reflux until clear (ca. 1 h), at which time it was cooled and the pH increased by addition of sodium hydroxide (NaOH, 5 N) which caused an off-white solid to precipitate. The solution was filtered and the resulting solid was dried in vacuo to give the desired product (88d) in 84% yield. LCMS (M+H) 215.1 calc for $C_7H_5BrFN_2$ 214.96. $^1$H NMR (400 MHz) MeOD: 8.06 (d, J=6.8 Hz, 1H), 8.03 (s, 1H), 7.37 (d, J=8.8 Hz, 1H).

Examples 89-93 are prepared using a procedure similar to that shown in Scheme 4 using 88 as the starting material.

| Example No. | Structure | Name | Molecular Formula | Theoretical (M + H) | Measured (M + H) |
|---|---|---|---|---|---|
| 89 | 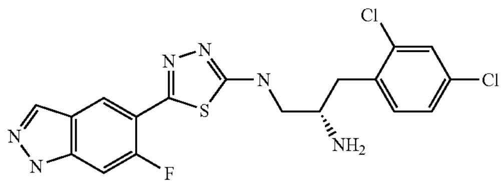 | N-((S)-2-amino-3-(2,4-dichlorophenyl)propyl)-5-(6-fluoro-1H-indazol-5-yl)-1,3,4-thiadiazol-2-amine | $C_{18}H_{15}Cl_2FN_6S$ | 437.05128 | 437.05061 |
| 90 | 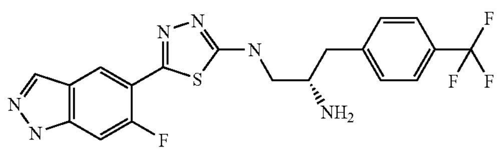 | N-((S)-2-amino-3-(4-(trifluoromethyl)phenyl)propyl)-5-(6-fluoro-1H-indazol-5-yl)-1,3,4-thiadiazol-2-amine | $C_{19}H_{16}F_4N_6S$ | 437.11660 | 437.11588 |
| 91 | 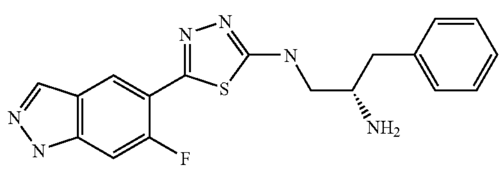 | N-((S)-2-amino-3-phenylpropyl)-5-(6-fluoro-1H-indazol-5-yl)-1,3,4-thiadiazol-2-amine | $C_{18}H_{17}FN_6S$ | 369.12922 | 369.12949 |
| 92 | 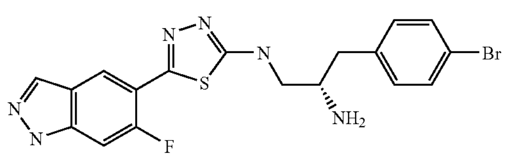 | N-((S)-2-amino-3-(4-bromophenyl)propyl)-5-(6-fluoro-1H-indazol-5-yl)-1,3,4-thiadiazol-2-amine | $C_{18}H_{16}BrFN_6S$ | 447.03973 | 447.03906 |
| 93 | | N-((S)-2-amino-3-(4-methoxyphenyl)propyl)-5-(6-fluoro-1H-indazol-5-yl)-1,3,4-thiadiazol-2-amine | C19H19FN6OS | 399 | 399 MS (API-ES) | acetamide (88b) (10 g, 41 mmol) was suspended in chloroform (90 mL) and acetic anhydride (11.5 mL, 122 mmol), potassium acetate (KOAc, 8.0 g, 81 mmol), 18-Crown-6 (0.54 g, 2 mmol) and i-amyl nitrite (12.3 mL, 92 mmol) were added sequentially. The mixture was heated at 65° C. for 24 h, cooled to room temperature and washed with sodium bicarbonate ($Na_2CO_3$ sat., 70 mL×3), dried over sodium sulfate ($Na_2SO_4$) and loaded directly onto silica gel. Column chromatography (0-20% EtOAc in hexanes) gave 1-(5-bromo-6-fluoro-1H-indazol-1-yl)ethanone (89c) in a 55% yield.

The resulting indazole was suspended in 10% HCl (70 mL) and methanol (ca. 20 mL) was added. The suspension was Example 94

5-(6-methyl-1H-indazol-5-yl)-1,3,4-thiadiazol-2-amine (94). This compound was prepared in a manner similar to that shown in Scheme 3, using 5-bromo-6-methyl-1H-indazole as the starting material, which was prepared in a manner similar to that of 5-bromo-6-fluoro-1H-indazole. The starting material was treated with t-butyl lithium and carbon dioxide to yield 6-methyl-1H-indazole-5-carboxylic acid, which was in turn treated with thiosemicarbazide and polyphosphoric acid to form 94.

Examples 95-100 are prepared using a similar procedure as shown in Scheme 4 using 94 as the starting material.

| Example No. | Structure | Name | Molecular Formula | Theoretical (M + H) | Measured (M + H) |
|---|---|---|---|---|---|
| 95 | 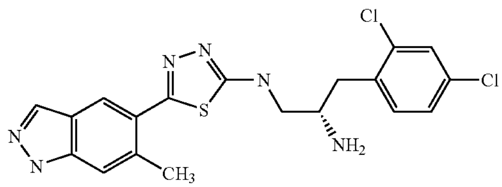 | N-((S)-2-amino-3-(2,4-dichlorophenyl)propyl)-5-(6-methyl-1H-indazol-5-yl)-1,3,4-thiadiazol-2-amine | C₁₉H₁₈Cl₂N₆S | 433.07635 | 433.07639 |
| 96 | 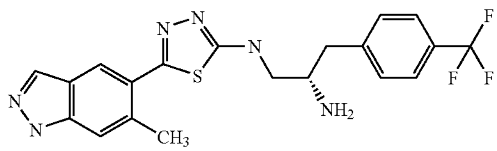 | N-((S)-2-amino-3-(4-(trifluoromethyl)phenyl)propyl)-5-(6-methyl-1H-indazol-5-yl)-1,3,4-thiadiazol-2-amine | C₂₀H₁₉F₃N₆S | 433.14168 | 433.14151 |
| 97 | 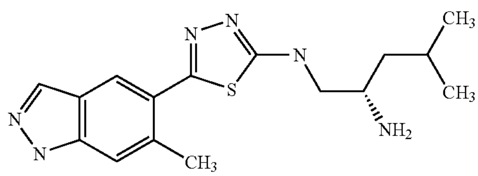 | N-((S)-2-amino-4-methylpentyl)-5-(6-methyl-1H-indazol-5-yl)-1,3,4-thiadiazol-2-amine | C₁₆H₂₂N₆S | 331.16994 | 331.16946 |
| 98 | 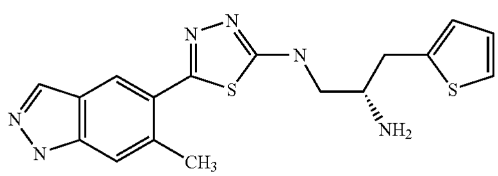 | N-((S)-2-amino-3-(thiophen-2-yl)propyl)-5-(6-methyl-1H-indazol-5-yl)-1,3,4-thiadiazol-2-amine | C₁₇H₁₈N₆S₂ | 371.11071 | 371.11037 |
| 99 | 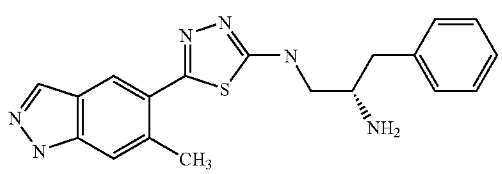 | N-((S)-2-amino-3-phenylpropyl)-5-(6-methyl-1H-indazol-5-yl)-1,3,4-thiadiazol-2-amine | C₁₉H₂₀N₆S | 365.15429 | 365.15384 |
| 100 | 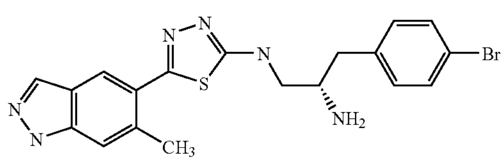 | N-((S)-2-amino-3-(4-bromophenyl)propyl)-5-(6-methyl-1H-indazol-5-yl)-1,3,4-thiadiazol-2-amine | C₁₉H₁₉BrN₆S | 443.06480 | 443.06411 |

Example 101

N—((S)-2-amino-3-methyl-3-phenylbutyl)-5-(3-methyl-1H-indazol-5-yl)-1,3,4-thiadiazol-2-amine (101). This compound was prepared in a manner similar to that shown in scheme 4. MS (API-ES) m/z (%): 393 (100%, M⁺+H).

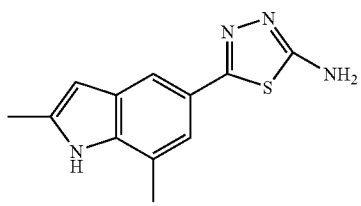

Example 102

5-(7-methyl-1H-indazol-5-yl)-1,3,4-thiadiazol-2-amine (102). This compound was prepared in a manner similar to the preparation of example 88 using commercially available 4-bromo-2,5-dimethylaniline as starting material. After an acylation step, N-(4-bromo-2,6-dimethylphenyl)acetamide was treated with isoamyl nitrite, and then 10% aqueous HCl to yield 5-bromo-7-methyl-1H-indazole. 5-bromo-7-methyl-1H-indazole was treated with t-butyl lithium and carbon dioxide to yield 6-methyl-1H-indazole-5-carboxylic acid, which is in turn was treated with thiosemicarbazide and polyphosphoric acid to form 5-(7-methyl-1H-indazol-5-yl)-1,3,4-thiadiazol-2-amine. MS (API-ES) m/z (%): 232 (100%, M⁺+1).

Examples 103-105 were prepared in a manner similar to the procedure shown in scheme 4 using 102 as the starting material.

Example 103

N—((S)-2-amino-3-(4-(trifluoromethyl)phenyl)propyl)-5-(7-methyl-1H-indazol-5-yl)-1,3,4-thiadiazol-2-amine (103). FTMS Theoretical (M+H) 433.14168, found 433.14158.

Example 104

N—((S)-2-amino-3-(4-chlorophenyl)propyl)-5-(7-methyl-1H-indazol-5-yl)-1,3,4-thiadiazol-2-amine (104). FTMS Theoretical (M+H) 399.11532, found 399.11591.

Example 105

N—((S)-2-amino-3-(2,4-dichlorophenyl)propyl)-5-(7-methyl-1H-indazol-5-yl)-1,3,4-thiadiazol-2-amine (105). FTMS Theoretical (M+H) 433.07635, found 433.07629.

Example 106

5-(7-chloro-1H-indazol-5-yl)-1,3,4-thiadiazol-2-amine: This compound was prepared similarly as 102 using commercial available 4-bromo-2-chloro-6-methylbenzenamine as starting material. MS (API-ES) m/z (%): 232 (100%, M$^+$+1).

Example 107

N—((S)-2-amino-3-(4-chlorophenyl)propyl)-5-(7-chloro-1H-indazol-5-yl)-1,3,4-thiadiazol-2-amine. This compound was prepared in a similar manner to that shown in scheme 4 using 106 as the starting material. FTMS Theoretical (M+H) 419.06070, found 419.06044.

Example 108

5-(1H-pyrazolo[3,4-c]pyridin-5-yl)-1,3,4-thiadiazol-2-amine. This example is made as shown in scheme 6.

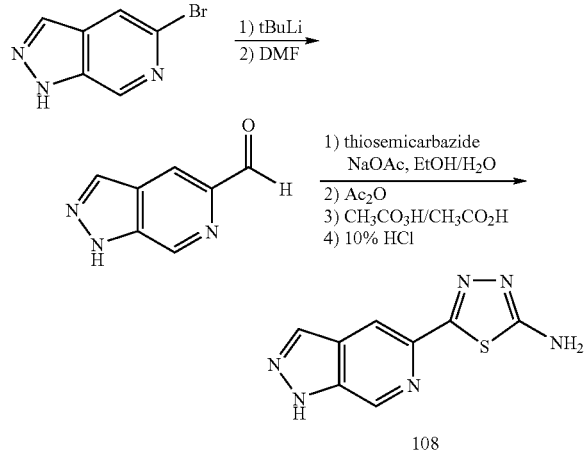

5-bromo-1H-pyrazolo[3,4-c]pyridine was prepared in a manner similar to that shown in Scheme 5 using commercially available 6-bromo-4-methylpyridin-3-amine as the starting material. After an acylation step, N-(6-bromo-4-methylpyridin-3-yl)acetamide was treated with isoamyl nitrite, then 10% aqueous HCl to yield 5-bromo-1H-pyrazolo[3,4-c]pyridine.

t-BuLi (27 mL, 1.7 M in pentane) was added to 100 mL of THF at −78° C. 5-bromo-1H-pyrazolo[3,4-c]pyridine (3.0 g, 15 mmol) was added dropwise to the solution in 50 ml of THF via addition funnel. The resulting mixture was stirred for 1 h, at which point DMF (6.0 mL, 76 mmol) was added dropwise. The reaction mixture was allowed to warm to room temperature and stirred 2 h. The reaction was then carefully quenched with aq. NH$_4$Cl and diluted with EtOAc. The resulting biphasic mixture was partitioned in a separatory funnel. The aqueous portion was extracted three tines with EtOAc, and the combined organic extracts were washed with brine and dried over MgSO$_4$. Filtration and concentration under reduced pressure, followed by flash chromatography on silica gel (100% CH$_2$Cl$_2$ to 7.5% MeOH/CH$_2$Cl$_2$), afforded the desired 1H-pyrazolo[3,4-c]pyridine-5-carbaldehyde (1.1 g, 50% yield) as a white solid. H$^1$ NMR (MeOD, 400 MHz) keto tautomer: 10.17 (s, 1H), 9.19 (s, 1H), 8.56 (s, 1H), 8.46 (s, 1H); enol tautomer: 9.00 (s, 1H), 8.25 (s, 1H), 8.05 (s, 2H), 5.73 (s, 1H). MS (API-ES) m/z (%): 147 (100%, M$^+$+1).

NaOAc (0.44 g) and thiosemicarbazide (1.1 g) were taken up in 30 mL of EtOH and heated to reflux. Water was added until the mixture became homogeneous. The heating bath was removed and 1H-pyrazolo[3,4-c]pyridine-5-carbaldehyde (1.1 g, 7.5 mmol) was added in one portion. The reaction mixture was returned to reflux and stirred for 3 h. As the reaction proceeded, a precipitate began to form. The reaction mixture was then cooled to room temperature and the precipitate was collected by filtration, then washed with MeOH and Et$_2$O and dried under high vacuum, affording 1.4 g of crude product that was carried on directly to the next step.

The product of the previous reaction was taken up in 15 mL of Ac$_2$O and heated to reflux for 30 min. Concentration under reduced pressure afforded a sticky solid. The sticky solid was taken up in 17 mL of acetic acid. Per-acetic acid (4.2 mL, 25% by wt in acetic acid) was added, and the mixture was heated to 65° C. After 90 min, the reaction was cooled to room temperature and a precipitate formed. The precipitate was collected by filtration, washed with H$_2$O and Et$_2$O, and dried under high vacuum. The dried precipitate was taken up in 30 mL of 10% HCl and heated to reflux to dissolve completely. The reaction mixture was then cooled to room temp and the pH of the solution was adjusted to 7.0 with 20% aq. NaOH. A white solid formed which was collected by filtration, washed with Et$_2$O, and dried under high vacuum, affording the desired 5-(1H-pyrazolo[3,4-c]pyridin-5-yl)-1,3,4-thiadiazol-2-amine 108 (0.88 g, 72% yield) as a largely insoluble white solid. MS (API-ES) m/z (%): 219 (100%, M$^+$+1).

Examples 109-111 were prepared in a similar manner to that shown in scheme 4 using 108 as the starting material.

Example 109

N—((S)-2-amino-3-(2,4-dichlorophenyl)propyl)-5-(1H-pyrazolo[3,4-c]pyridin-5-yl)-1,3,4-thiadiazol-2-amine. FTMS Theoretical (M+H) 420.05595, found 420.05603.

Example 110

N—((S)-2-amino-3-(4-bromophenyl)propyl)-5-(1H-pyrazolo[3,4-c]pyridin-5-yl)-1,3,4-thiadiazol-2-amine. MS (API-ES) m/z (%): 430 (100%, M$^+$+1), 432(96%, M$^+$+3).

Example 111

N—((S)-2-amino-3-(4-(trifluoromethyl)phenyl)propyl)-5-(1H-pyrazolo[3,4-c]pyridin-5-yl)-1,3,4-thiadiazol-2-amine. MS (API-ES) m/z (%): 420 (100%, M$^+$+1).

Example 112

N—((S)-2-amino-3-(3-(trifluoromethyl)phenyl)propyl)-5-(3-methyl-1H-pyrazolo[3,4-b]pyridin-5-yl)-1,3,4-thiadiazol-2-amine. This compound was prepared according to the procedure shown in scheme 7.

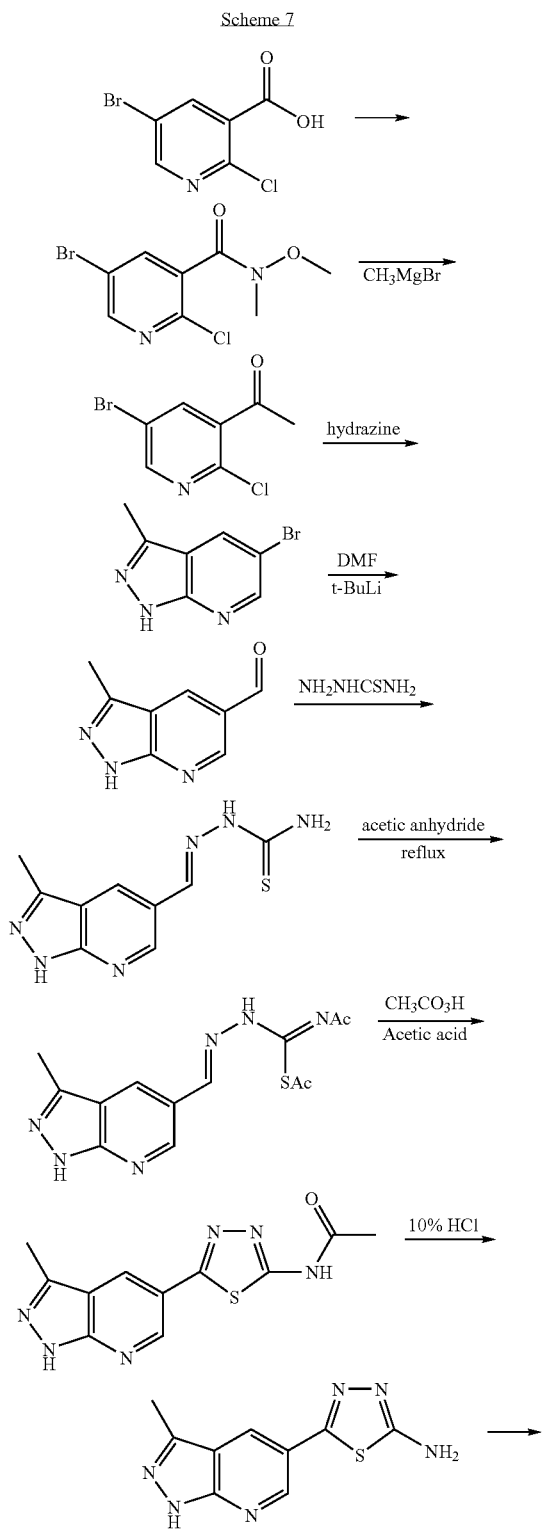

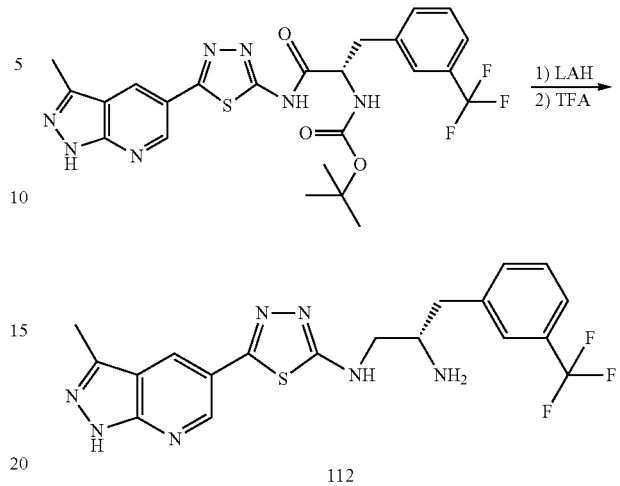

5-Bromo-2-chloro-N-methoxy-N-methylnicotinamide: Commercial available 5-bromo-2-chloronicotinic acid (1a) (15.0 g, 63.44 mmol) was dissolved in 50 ml DMF and N,N'-carbonyldiimidazole (11.30 g, 69.78 mmol) was added portion wise. The resulting solution was stirred for 10 min and then N,O-dimethylhydroxylamine hydrochloride was added. After one hour, DMF was removed via rotatory evaporation at a reduced pressure and the resulting residue was diluted with saturated sodium bicarbonate and extracted by dichloromethane in a separation funnel. The combined organic layer was washed with brine and dried over sodium sulfate. Removal of the solvent gave the product in quantitative yield. The product was used directly for the next step without further purification.

1-(5-Bromo-2-chloropyridin-3-yl)ethanone: Starting material 5-bromo-2-chloro-N-methoxy-N-methylnicotinamide (5.0 g, 17.89 mmol) was charged into a 250 ml round bottom flask and the flask was chilled to −78° C. Methyl magnesium bromide 96.5 ml, 19.68 mmol) in 5 ml THF was added dropwise via addition funnel. The resulting mixture was allowed to stir for 3 hours at −78° C. After removing the THF solvent via rotatory evaporation under reduced pressure, the reaction mixture was partitioned between ethylacetate and saturated aqueous sodium bicarbonate. After removing the ethylacetate, the resulting crude product was subject to a silica gel column with 20% ethylacetate in hexane. The resulting product (2.28 g, y=54.3%) was used for the following step.

5-Bromo-3-methyl-1H-pyrazolo[3,4-b]pyridine: Starting material 1-(5-bromo-2-chloropyridin-3-yl)ethanone (5.8 g, 24.7 mmol) and 100 ml anhydrous hydrazine was charged into 500 ml round bottom flask and the resulting mixture was allowed to stir at room temperature for overnight. After removing the excess hydrazine via rotatory evaporation under reduced pressure, the remaining residue was diluted with distilled water and solid was appeared. After filtering the water, the resulting solid was taken up in ethylacetate and saturated aqueous sodium bicarbonate and was extracted by ethylacetate twice. The combined organic layer was washed with water and brine and dried over sodium sulfate. The crude product was eluted through a short silica gel column (3 inch in length) with ethylacetate as a white solid (4.0 g, y=77%).

3-Methyl-1H-pyrazolo[3,4-b]pyridine-5-carbaldehyde:
80 ml anhydrous THF were charged into a 250 ml round bottom flask and was chilled to −78° C. t-BuLi (1.70 M in THF, 17.6 ml, 30 mmol) was added to the flask via syringe. After stirring for 5 min, 5-bromo-3-methyl-1H-pyrazolo[3,4-b]pyridine (2.12 g, 10 mmol) was added dropwise via syringe. After 30 min, DMF (3.65 g, 50 mmol) in 20 ml THF was added dropwise and the mixture was stirred for overnight. The reaction was quenched by saturated aqueous ammonium chloride. After evaporating the excess THF, the reaction mixture was extracted by ethylacetate twice. The combined organic layer was washed with brine once and dried over sodium sulfate. The crude product was chromatographed with 50% ethylacetate in hexane to afford the desired product (0.23 g, y=20.5%).

1-((3-Methyl-1H-pyrazolo[3,4-b]pyridin-5-yl)methylene)thiosemicarbazide: Sodium acetate (166 mg, 2.02 mmol), thiosemicarbazide (333 mg, 3.66 mmol), 100 ml ethanol and 2 ml distilled water were charged into a 250 ml round bottom flask. The resulting suspension was heated to 80° C. until it becomes a clear solution. The reaction was then cooled down to room temperature and the resulting mixture was added into a 250 ml round bottom flask containing 3-methyl-1H-pyrazolo[3,4-b]pyridine-5-carbaldehyde (333 mg, 2.1 mmol). After the addition, the resulting mixture was heated to 80° C. for 16 hours. The mixture was cooled to room temperature and solid was precipitated out. The solid was filtered off and washed with ether (50 ml). The product (500 mg, y=95%) was used directly for the next step without further purification.

1-Acetyl-3-((E)-(3-methyl-1H-pyrazolo[3,4-b]pyridin-5-yl)methyleneamino)isothiourea: The staring material 1-((3-methyl-1H-pyrazolo[3,4-b]pyridin-5-yl)methylene)thiosemicarbazide (500 mg, 2.0 mmol) and acetic anhydride (20 ml) was mixed and heated to 80° C. for 1 hour. The reaction mixture was then cooled down to room temperature. The yellow solid was precipitated out and was filtered off. The yellow solid was washed with ether (50 ml). The product was obtained in quantitative yield and used for the next step without further purification.

N-(5-(3-Methyl-1H-pyrazolo[3,4-b]pyridin-5-yl)-1,3,4-thiadiazol-2-yl)acetamide: The starting material 1-acetyl-3-((E)-(3-methyl-1H-pyrazolo[3,4-b]pyridin-5-yl)methyleneamino)isothiourea (5 g) (80 mg, 0.22 mmol) was taken up in 5 ml acetic acid and 1.2 ml peracetic acid in a round bottom flask. The mixture was heated to 60° C. After 15 min, the product was precipitated out. The solid was filtered off and washed with ether (50 ml). The yield for this reaction was quantitative and the product was used for the next step without further purification.

5-(3-Methyl-1H-pyrazolo[3,4-b]pyridin-5-yl)-1,3,4-thiadiazol-2-amine: The starting material N-(5-(3-methyl-1H-pyrazolo[3,4-b]pyridin-5-yl)-1,3,4-thiadiazol-2-yl)acetamide (60 mg, 0.18 mmol) and 20 ml 10% HCl solution was mixed in a 100 ml round bottom flask. The resulting mixture was heated for 1 hour. The reaction mixture was cooled and neutralized by 20% sodium hydroxide solution until the solution turns into basic. The solution was partitioned between ethylacetate and saturated aqueous sodium bicarbonate. The organic layer was washed by brine solution and was dried by sodium sulfate. The resulting product (50 mg, y=90%) was used for the next step without further purification.

Finally, 5-(3-methyl-1H-pyrazolo[3,4-b]pyridin-5-yl)-1,3,4-thiadiazol-2-amine was transformed to 112 in a manner similar to the procedure shown in scheme 4.

Example 113

5-(4-methyl-1H-indazol-5-yl)-1,3,4-thiadiazol-2-amine.

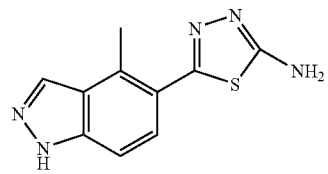

This compound was prepared in a manner similar to the preparation of 88 using commercially available 4-bromo-2,3-dimethylaniline as starting material. After an acylation step, N-(4-bromo-2,3-dimethylphenyl)acetamide was treated with isoamyl nitrite, then 10% aqueous HCl to yield 5-bromo-4-methyl-1H-indazole. 5-bromo-4-methyl-1H-indazole was treated with t-butyl lithium and carbon dioxide to yield 4-methyl-1H-indazole-5-carboxylic acid, which in turn was treated with thiosemicarbazide and polyphosphoric acid to form 5-(4-methyl-1H-indazol-5-yl)-1,3,4-thiadiazol-2-amine. MS (API-ES) m/z (%): 232 (100%, M$^+$+1).

Examples 114-116 were prepared using a similar procedure as that shown in scheme 4 using 113 as the starting material.

Example 114

N—((S)-2-amino-3-(4-(trifluoromethyl)phenyl)propyl)-5-(4-methyl-1H-indazol-5-yl)-1,3,4-thiadiazol-2-amine. FTMS Theoretical (M+H) 433.1416, found 433.1415.

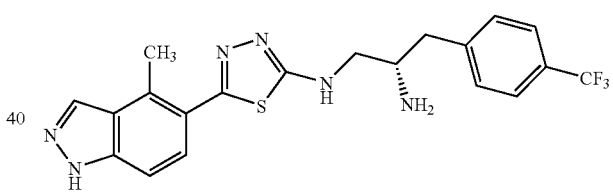

Example 115

N—((S)-2-amino-3-(4-chlorophenyl)propyl)-5-(4-methyl-1H-indazol-5-yl)-1,3,4-thiadiazol-2-amine. FTMS Theoretical (M+H) 399.11532, found 399.11524.

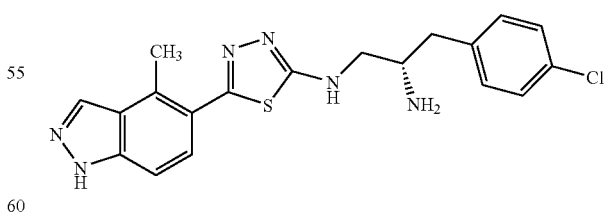

Example 116

N—((S)-2-amino-3-(2,4-dichlorophenyl)propyl)-5-(4-methyl-1H-indazol-5-yl)-1,3,4-thiadiazol-2-amine. FTMS Theoretical (M+H) 433.07635, found 433.07693.

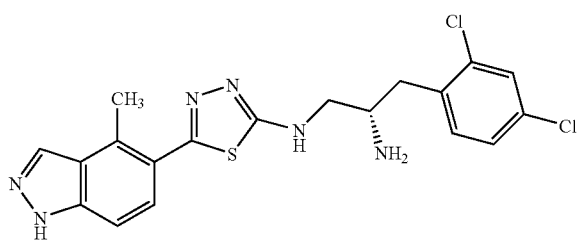

Example 117

5-(3-cyclopropyl-1H-indazol-5-yl)-1,3,4-thiadiazol-2-amine. This compound was prepared in a manner similar to the procedure shown in scheme 3. The first step used cyclopropyl magnesium bromide instead of methyl magnesium bromide. MS (API-ES) m/z (%): 258 (100%, M$^+$+1).

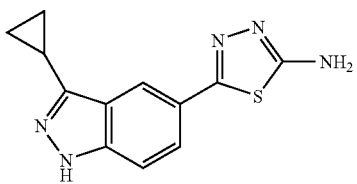

Examples 118-120 were prepared in a manner similar to that shown in scheme 4 using 117 as the starting material.

Example 118

N—((S)-2-amino-3-phenylpropyl)-5-(3-cyclopropyl-1H-indazol-5-yl)-1,3,4-thiadiazol-2-amine. MS (API-ES) m/z (%): 381 (100%, M$^+$+H).

Example 119

N—((S)-2-amino-3-(4-chlorophenyl)propyl)-5-(3-cyclopropyl-1H-indazol-5-yl)-1,3,4-thiadiazol-2-amine. MS (API-ES) m/z (%): 425 (100%, M$^+$+H).

Example 120

N—((S)-2-amino-3-(4-(trifluoromethyl)phenyl)propyl)-5-(3-cyclopropyl-1H-indazol-5-yl)-1,3,4-thiadiazol-2-amine. MS (API-ES) m/z (%): 422 (100%, M$^+$+H).

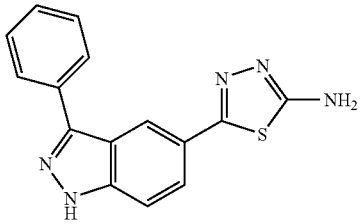

Example 121

5-(3-phenyl-1H-indazol-5-yl)-1,3,4-thiadiazol-2-amine. This compound was prepared in a manner similar to that shown in scheme 3, except the first step used phenylmagnesium bromide instead of methyl magnesium bromide. MS (API-ES) m/z (%): 294 (100%, M$^+$+1).

Examples 122-124 were prepared in a manner similar to that shown in scheme 4 using 117 as the starting material.

Example 122

N—((S)-2-amino-4-methylpentyl)-5-(3-phenyl-1H-indazol-5-yl)-1,3,4-thiadiazol-2-amine. FTMS Theoretical (M+H) 393.1856, found 393.1853.

Example 123

N—((S)-2-amino-3-(3-(trifluoromethyl)phenyl)propyl)-5-(3-phenyl-1H-indazol-5-yl)-1,3,4-thiadiazol-2-amine. FTMS Theoretical (M+H) 495.1573, found 495.1575.

Example 124

N—((S)-2-amino-3-phenylpropyl)-5-(3-phenyl-1H-indazol-5-yl)-1,3,4-thiadiazol-2-amine. FTMS Theoretical (M+H) 427.1699, found 427.1696.

Example 125

5-(3-ethyl-1H-indazol-5-yl)-1,3,4-thiadiazol-2-amine.

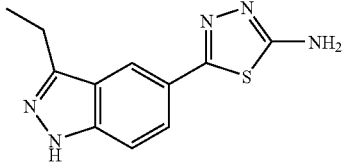

The synthesis of 125 is illustrated in scheme 8.

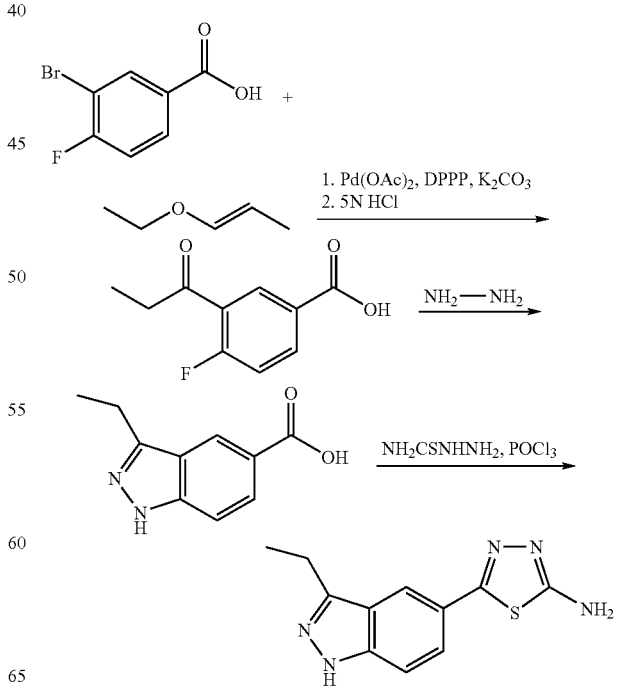

4-Fluoro-3-propionylbenzoic acid was synthesized by treating the commercial available 3-bromo-4-fluorobenzoic acid with 1-ethoxyprop-1-ene (6 equivalents), palladium acetate (0.03 equivalents), 1,3-Bis-(diphenylphosphino)-propane (0.06 equivalents) and potassium carbonate (1.2 equivalents) in DMF and water under microwave at 130° C. for 3 hours following with an acid treatment. 3-Ethyl-1H-indazole-5-carboxylic acid was obtained by treating 4-Fluoro-3-propionylbenzoic acid with hydrazine under microwave at 160° C. for half an hour. 5-(3-ethyl-1H-indazol-5-yl)-1,3,4-thiadiazol-2-amine was prepared in a manner similar to that shown in scheme 3 with POCl$_3$ and thiosemicarbazide. MS (API-ES) m/z (%): 246 (100%, M$^+$+1).

Example 126

N—((S)-2-amino-3-phenylpropyl)-5-(3-ethyl-1H-indazol-5-yl)-1,3,4-thiadiazol-2-amine. This compound was prepared in a manner similar to the procedure shown in scheme 4, except using 125 as the starting material. MS (API-ES) m/z (%): 379 (100%, M$^+$+1).

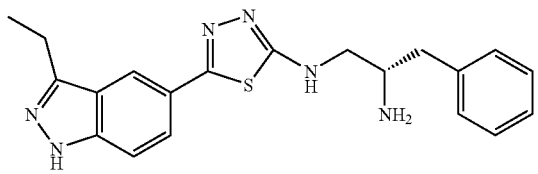

Examples 127-128 were synthesized in a manner similar to that shown in scheme 4.

Example 127

N—((S)-2-amino-5-phenylpentyl)-5-(3-methyl-1H-indazol-5-yl)-1,3,4-thiadiazol-2-amine. MS (API-ES) m/z (%): 393 (100%, M$^+$+1).

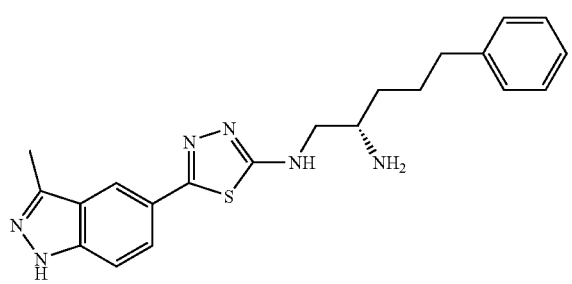

Example 128

N—((R)-2-amino-3-(benzyloxy)propyl)-5-(3-methyl-1H-indazol-5-yl)-1,3,4-thiadiazol-2-amine. MS (API-ES) m/z (%): 395 (100%, M$^+$+1).

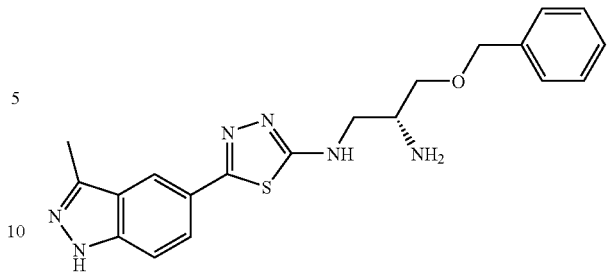

Examples 129-134 were prepared according to a general procedure that used LAH to reduce the amide bond and the Boc group at the same time at 60° C. instead of at 0° C., as shown in Scheme 4. The crude product (1 mmol) from the amide bond formation as shown in scheme 4 was dissolved in 5 ml of THF and 6 ml of LAH was added (1M in THF). The reaction mixture was heated in a sealed tube to 60° C. for 2 h and cooled to room temperature after that. The reaction mixture was diluted with 20 ml THF and poured into a mixture of 10 g Na$_2$SO$_4$ 10H$_2$O in 30 ml THF and stirring was continued for 20 min. The reaction mixture was filtered, washed, dried over MgSO$_4$ and concentrated. The reaction product was purified on prep-TLC (12% MeOH in CH$_2$Cl$_2$).

Example 129

N—((S)-3-(4-chlorophenyl)-2-(methylamino)propyl)-5-(3-methyl-1H-indazol-5-yl)-1,3,4-thiadiazol-2-amine. MS (API-ES) m/z (%): 413 (100%, M$^+$+1), 415 (45%, M$^+$+3), 414 (30%, M$^+$+2).

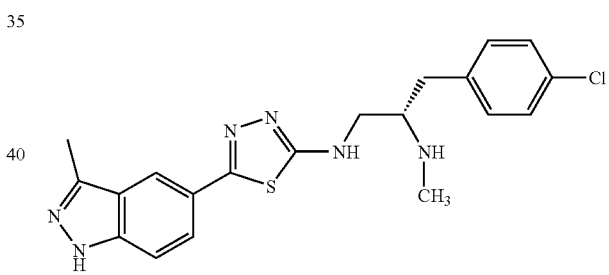

Example 130

5-(3-methyl-1H-indazol-5-yl)-N—((S)-2-(methylamino)-3-(4-(trifluoromethyl)phenyl)propyl)-1,3,4-thiadiazol-2-amine. MS (API-ES) m/z (%): 447 (100%, M$^+$+1), 448 (20%, M$^+$+2).

Example 131

5-(3-methyl-1H-indazol-5-yl)-N—((S)-2-(methylamino)-3-(3-(trifluoromethyl)phenyl)propyl)-1,3,4-thiadiazol-2-amine. MS (API-ES) m/z (%): 447 (100%, M$^+$+1), 448 (20%, M$^+$+2).

Example 132

N—((S)-3-(2,4-dichlorophenyl)-2-(methylamino)propyl)-5-(1H-indazol-5-yl)-1,3,4-thiadiazol-2-amine. FTMS Theoretical (M+H) 433.0764, found 433.0760.

Example 133

N—((S)-3-(4-chlorophenyl)-2-(methylamino)propyl)-5-(1H-indazol-5-yl)-1,3,4-thiadiazol-2-amine. FTMS Theoretical (M+H) 399.1153, found 399.1150.

Example 134

5-(1H-indazol-5-yl)-N—((S)-2-(methylamino)-3-(4-(trifluoromethyl)phenyl)propyl)-1,3,4-thiadiazol-2-amine. FTMS Theoretical (M+H) 433.1417, found 433.1411.

Examples 135-144 were prepared using 37 as the starting material via a reductive alkylation procedure. (S)—N-[5-(3-Methyl-1H-indazol-5-yl)-[1,3,4]thiadiazol-2-yl]-3-(3-trifluoromethyl-phenyl)-propane-1,2-diamine (15 mg) was dissolved in 0.1 ml of MeOH and 5 drops (from a Pasteur Pipette) of AcOH was added. 6 equivalents of the carbonyl compound was added and stirring was continued for 30 min. 3 equiv of Na(OAc)$_3$BH was added and stirring was continued over night. The reaction mixture was either loaded without further purification on a prep-TLC plate or a prep-HPLC for purification purposes.

Example 135

N-isopropyl-1-(5-(3-methyl-1H-indazol-5-yl)-1,3,4-thiadiazol-2-ylamino)-3-(3-(trifluoromethyl)phenyl)propan-2-aminium chloride. MS (API-ES) m/z (%): 475 (100%, M$^+$+1), 497 (5%, M$^+$+23).

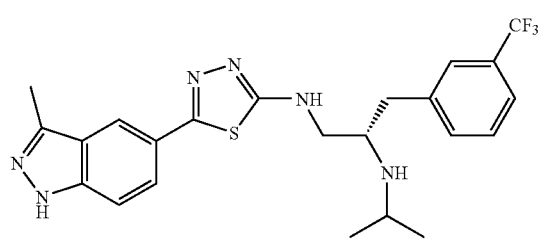

Example 136

N-(1-(5-(3-methyl-1H-indazol-5-yl)-1,3,4-thiadiazol-2-ylamino)-3-(3-(trifluoromethyl)phenyl)propan-2-yl)-N-propylpropan-1-aminium 2,2,2-trifluoroacetate: MS (API-ES) m/z (%): 517 (100%, M$^+$+1).

Example 137

N-(1-(5-(3-methyl-1H-indazol-5-yl)-1,3,4-thiadiazol-2-ylamino)-3-(3-(trifluoromethyl)phenyl)propan-2-yl)heptan-1-aminium 2,2,2-trifluoroacetate. MS (API-ES) m/z (%): 531 (100%, M$^+$+1), 532 (30%, M$^+$+2).

Example 138

N-heptyl-N-(1-(5-(3-methyl-1H-indazol-5-yl)-1,3,4-thiadiazol-2-ylamino)-3-(3-(trifluoromethyl)phenyl)propan-2-yl)heptan-1-aminium 2,2,2-trifluoroacetate. MS (API-ES) m/z (%): 629 (100%, M$^+$+1), 630 (30%, M$^+$+2).

Example 139

N-(1-(5-(3-methyl-1H-indazol-5-yl)-1,3,4-thiadiazol-2-ylamino)-3-(3-(trifluoromethyl)phenyl)propan-2-yl)cyclohexanaminium chloride. MS (API-ES) m/z (%): 515 (100%, M$^+$+1), 516 (30%, M$^+$+2).

Example 140

N-(4-hydroxybenzyl)-1-(5-(3-methyl-1H-indazol-5-yl)-1,3,4-thiadiazol-2-ylamino)-3-(3-(trifluoromethyl)phenyl)propan-2-aminium 2,2,2-trifluoroacetate. MS (API-ES) m/z (%): 539 (100%, M$^+$+1), 561 (10%, 2M$^+$+23).

Example 141

N-(4-methoxybenzyl)-1-(5-(3-methyl-1H-indazol-5-yl)-1,3,4-thiadiazol-2-ylamino)-3-(3-(trifluoromethyl)phenyl)propan-2-aminium 2,2,2-trifluoroacetate. MS (API-ES) m/z (%): 553 (100%, M$^+$+1).

Example 142

N-(cyclohexylmethyl)-1-(5-(3-methyl-1H-indazol-5-yl)-1,3,4-thiadiazol-2-ylamino)-3-(3-(trifluoromethyl)phenyl)propan-2-aminium 2,2,2-trifluoroacetate. MS (API-ES) m/z (%): 529 (100%, M$^+$+1), 530 (30%, M$^+$+2).

Example 143

N-(3-(trifluoromethyl)benzyl)-1-(5-(3-methyl-1H-indazol-5-yl)-1,3,4-thiadiazol-2-ylamino)-3-(3-(trifluoromethyl)phenyl)propan-2-aminium 2,2,2-trifluoroacetate. MS (API-ES) m/z (%): 591 (100%, M$^+$+1) 592 (30%, M$^+$+2).

Example 144

N-(furan-2-ylmethyl)-1-(5-(3-methyl-1H-indazol-5-yl)-1,3,4-thiadiazol-2-ylamino)-3-(3-(trifluoromethyl)phenyl)propan-2-aminium 2,2,2-trifluoroacetate. MS (API-ES) m/z (%): 513 (100%, M$^+$+1).

Examples 145-155 were prepared in a similar manner to the compounds shown in scheme 4 except that 5-isoquinolin-6-yl-[1,3,4]thiadiazol-2-yl-amine (see scheme 1) was used as the starting material. These compounds were obtained after 5-isoquinolin-6-yl-[1,3,4]thiadiazol-2-yl-amine was coupled with the corresponding Boc protected amino acids, then a LAH reduction procedure followed with an acid treatment step to remove the Boc group.

Example 145

N—((S)-2-amino-3-(4-methoxyphenyl)propyl)-5-(isoquinolin-6-yl)-1,3,4-thiadiazol-2-amine. FTMS Theoretical (M+H$^+$) 392.15396 found 392.15448.

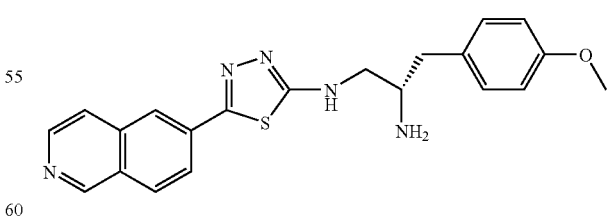

Example 146

N—((S)-2-amino-3-(3-(trifluoromethyl)phenyl)propyl)-5-(isoquinolin-6-yl)-1,3,4-thiadiazol-2-amine. FTMS Theoretical (M+H$^+$) 430.13078 found 430.13139.

Example 147

N—((S)-2-amino-3-(4-(trifluoromethyl)phenyl)propyl)-5-(isoquinolin-6-yl)-1,3,4-thiadiazol-2-amine. FTMS Theoretical (M+H$^+$) 430.13078 found 430.13048.

Example 148

N—((S)-2-amino-3-(3-methoxyphenyl)propyl)-5-(isoquinolin-6-yl)-1,3,4-thiadiazol-2-amine. FTMS Theoretical (M+H$^+$) 392.15396 found 392.15439.

Example 149

N—((S)-2-amino-3-(2,4-dichlorophenyl)propyl)-5-(isoquinolin-6-yl)-1,3,4-thiadiazol-2-amine. FTMS Theoretical (M+H$^+$) 430.06545 found 430.06551.

Example 150

N—((S)-2-amino-3-(4-dichlorophenyl)propyl)-5-(isoquinolin-6-yl)-1,3,4-thiadiazol-2-amine. FTMS Theoretical (M+H$^+$) 396.10442 found 396.10486.

Example 151

N—((S)-2-amino-3-(3,5-difluorophenyl)propyl)-5-(isoquinolin-6-yl)-1,3,4-thiadiazol-2-amine: FTMS Theoretical (M+H$^+$) 398.12455 found 398.12463.

Example 152

N—((S)-2-amino-3-m-tolylpropyl)-5-(isoquinolin-6-yl)-1,3,4-thiadiazol-2-amine: FTMS Theoretical (M+H$^+$) 376.15904 found 376.15917.

Example 153

N—((S)-2-amino-3-(3-fluorophenyl)propyl)-5-(isoquinolin-6-yl)-1,3,4-thiadiazol-2-amine. FTMS Theoretical (M+H$^+$) 380.13397 found 380.13423.

Example 154

N—((S)-2-amino-3-p-tolylpropyl)-5-(isoquinolin-6-yl)-1,3,4-thiadiazol-2-amine. FTMS Theoretical (M+H$^+$) 376.15904 found 376.15970.

Example 155

N—((R)-2-amino-3-(4-(trifluoromethyl)phenyl)propyl)-5-(isoquinolin-6-yl)-1,3,4-thiadiazol-2-amine. FTMS Theoretical (M+H$^+$) 430.13078 found 430.13096.

Examples 156-162 were synthesized in a manner similar to the compounds shown in scheme 4, except 69 5-(1H-indazol-5-yl)-1,3,4-thiadiazol-2-amine was used as the starting material.

Example 156

N—((S)-2-amino-3-(4-fluorophenyl)propyl)-5-(1H-indazol-5-yl)-1,3,4-thiadiazol-2-amine. FTMS Theoretical (M+H$^+$) 369.12922 found 369.12939.

Example 157

N—((S)-2-amino-2-(2,3-dihydro-1H-inden-2-yl)ethyl)-5-(1H-indazol-5-yl)-1,3,4-thiadiazol-2-amine. FTMS Theoretical (M+H$^+$) 377.15429 found 377.15422.

Example 158

N—((S)-2-amino-3-(pyridin-2-yl)propyl)-5-(1H-indazol-5-yl)-1,3,4-thiadiazol-2-amine. FTMS Theoretical (M+H$^+$) 352.13389 found 352.13446.

Example 159

5-(1H-indazol-5-yl)-N-(((2S,4S)-4-phenylpyrrolidin-2-yl)methyl)-1,3,4-thiadiazol-2-amine. FTMS Theoretical (M+H$^+$) 377.15429 found 377.15448.

Example 160

4-((S)-3-(5-(1H-indazol-5-yl)-1,3,4-thiadiazol-2-ylamino)-2-aminopropyl)-2-chlorophenol. FTMS Theoretical (M+H$^+$) 401.09460 found 401.09510.

Example 161

3-((S)-3-(5-(1H-indazol-5-yl)-1,3,4-thiadiazol-2-ylamino)-2-aminopropyl)-1H-indol-6-ol. FTMS Theoretical (M+H$^+$) 406.14450 found 406.14507.

Example 162

N—((S)-2-amino-3-(pyridin-4-yl)propyl)-5-(1H-indazol-5-yl)-1,3,4-thiadiazol-2-amine. FTMS Theoretical (M+H$^+$) 352.13389 found 352.13465.

Example 163

N-(((2S,4R)-4-(benzyloxy)pyrrolidin-2-yl)methyl)-5-(1H-indazol-5-yl)-1,3,4-thiadiazol-2-amine. MS (API-ES) m/z (%): 407.1 (100%, M$^+$+1).

Examples 164-168 are prepared in a manner similar to examples 145-155.

Example 164

N-(((2S,4R)-4-(benzyloxy)pyrrolidin-2-yl)methyl)-5-(isoquinolin-6-yl)-1,3,4-thiadiazol-2-amine. MS (API-ES) m/z (%): 418.2 (100%, M$^+$+1).

Example 165

5-(isoquinolin-6-yl)-N-(((3S,4R)-4-(4-(trifluoromethyl)phenyl)pyrrolidin-3-yl)methyl)-1,3,4-thiadiazol-2-amine. MS (API-ES) m/z (%): 456.1 (100%, M$^+$+1).

Example 166

N-(((1R,2S)-1-amino-2-phenylcyclopropyl)methyl)-5-(isoquinolin-6-yl)-1,3,4-thiadiazol-2-amine. MS (API-ES) m/z (%): 374.1 (100%, M$^+$+1).

Example 167

N—((S)-2-amino-3-(2-fluoro-4-(trifluoromethyl)phenyl)propyl)-5-(isoquinolin-6-yl)-1,3,4-thiadiazol-2-amine. MS (API-ES) m/z (%): 448.1 (100%, M$^+$+1).

Example 168

N—((S)-1-(5-(isoquinolin-6-yl)-1,3,4-thiadiazol-2-ylamino)-3-(4-(trifluoromethoxy)phenyl)propan-2-yl)acetamide. MS (API-ES) m/z (%): 488.14 (100%, M$^+$+1).

Example 169

N—((S)-2-amino-3-(4-(trifluoromethyl)phenyl)propyl)-5-(1,6-naphthyridin-2-yl)-1,3,4-thiadiazol-2-amine. This compound was synthesized in a manner similar to that shown in scheme 4 using 5-(1,6-naphthyridin-2-yl)-1,3,4-thiadiazol-2-amine as the starting material, which was prepared from commercially available 1,6-naphthyridine-2-carboxylic acid in a manner similar to the procedure shown in scheme 1. MS (API-ES) m/z (%): 431.1 (100%, M$^+$+1).

Examples 170-173 were synthesized in a manner similar to the compounds shown in scheme 4.

Example 170

N—((S)-2-amino-2-((R)-2,3-dihydro-1H-inden-1-yl)ethyl)-5-(3-methyl-1H-indazol-5-yl)-1,3,4-thiadiazol-2-amine. FTMS Theoretical (M+H$^+$) 391.16994 found 391.17051.

Example 171

5-(3-methyl-1H-indazol-5-yl)-N-((3-phenylpiperidin-2-yl)methyl)-1,3,4-thiadiazol-2-amine. FTMS Theoretical (M+H$^+$) 405.18559 found 405.18614.

Example 172

N—((S)-2-amino-3-(4-bromophenyl)propyl)-5-(3-methyl-1H-indazol-5-yl)-1,3,4-thiadiazol-2-amine. MS (API-ES) m/z (%): 431 (100%, M$^+$+1).

Example 173

N—((S)-2-amino-3-(thiophen-3-yl)propyl)-5-(3-methyl-1H-indazol-5-yl)-1,3,4-thiadiazol-2-amine. MS (API-ES) m/z (%): 371 (100%, M$^+$+1).

Examples 174-176 were synthesized in a manner similar to examples 145-155.

Example 174

5-(isoquinolin-6-yl)-N-(2-(methylamino)ethyl)-1,3,4-thiadiazol-2-amine. MS (API-ES) m/z (%): 400.1 (100%, M$^+$+1).

Example 175

N-(2-((4-(trifluoromethyl)benzyl)(methyl)amino)ethyl)-5-(isoquinolin-6-yl)-1,3,4-thiadiazol-2-amine. MS (API-ES) m/z (%): 444.2 (100%, M$^+$+1).

Example 176

N-((2S,3S)-2-amino-3-(4-(trifluoromethyl)phenyl)butyl)-5-(isoquinolin-6-yl)-1,3,4-thiadiazol-2-amine. MS (API-ES) m/z (%): 444 (100%, M$^+$+1).

Examples 177-178 were synthesized in a manner similar to that shown in scheme 4 using 69 5-(1H-indazol-5-yl)-1,3,4-thiadiazol-2-amine as the starting material.

Example 177

N-((2S,3S)-2-amino-3-(4-(trifluoromethyl)phenyl)butyl)-5-(1H-indazol-5-yl)-1,3,4-thiadiazol-2-amine. MS (API-ES) m/z (%): 433 (100%, M$^+$+1).

Example 178

N-((2S,3R)-2-amino-3-(4-(trifluoromethyl)phenyl)butyl)-5-(1H-indazol-5-yl)-1,3,4-thiadiazol-2-amine. MS (API-ES) m/z (%): 433 (100%, M$^+$+1).

Example 179

5-(3-methylisoquinolin-6-yl)-1,3,4-thiadiazol-2-amine. This compound was prepared in a manner similar to compounds shown in scheme 1, except using 3-methylisoquinolin-6-carboxylic acid as the starting material. MS (API-ES) m/z (%): 243 (100%, M$^+$+1).

Example 180

N—((S)-2-amino-3-(4-(trifluoromethyl)phenyl)propyl)-5-(3-methylisoquinolin-6-yl)-1,3,4-thiadiazol-2-amine. This compound was prepared in a manner similar to compounds shown in scheme 4, except using 179 as the starting material. MS (API-ES) m/z (%): 444 (100%, M$^+$+1).

5.1 PKB Assay Testing

Kinase assay for evaluating PKB activity comprises active PKB enzymes, a PKB specific substrate and P$^{33}$-labelded ATP. Two form of PKBα enzymes were used, the full length PKBα and a kinase domain of PKBα with pleckstrin domain (amino acids 1-117) deleted. Both PKB enzymes were from Upstate cell signaling solutions (Cat.#14-276 and 14-341. The PKB substrate used is a synthetic peptide (ARKRERTYSFGHHA) as described in Obata et al., J. Biol. Chem. 275, 36108-36115. The phosphorylated substrate was captured by phosphocellulose membrane filter plate (MILLIPORE) and measured by Wallac Microbeta liquid scintillation counter (Perkin Elmer). The compounds of Examples 1-180 exhibited PKBα kinase activity with IC$_{50}$ values less than 10 µM.

PKB activity in cells was assayed in a PTEN null human breast tumor cell line MDA-MB-468. The phosphorylation status of PKB substrate FKHRL1, GSK3a/b, and Tuberin were measured by immunoassays utilizing phospho-specific antibodies (Cell signaling technology). The compounds of Examples 1-180 exhibited PKB kinase activity with IC$_{50}$ values less than 10 µM.

The effect of PKB inhibition on cell viability was measured in a range of human tumor cell lines including but not limiting to MDA-MB-468, MDA-MB-231, U87-MG, LN-229, PC3, DU145. The cells were treated in regular growth media for 72 hours and cell viability was measured by Alamar Blue (Biosource).

The foregoing has demonstrated the pertinent and important features of the present invention. Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A compound of Formula I

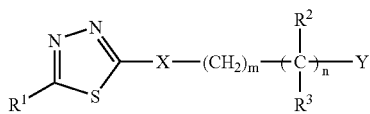

wherein:
- Y is —N(R⁴)R⁵;
- X is N(R⁶);
- $R^1$ is an aryl or heteroaryl;
- $R^2$ is H;
- $R^3$ is aryl, heteroaryl, cycloalkyl, or heterocyclyl;
- $R^4$ is —H;
- $R^5$ and $R^6$ are independently selected from —H and $C_1$-$C_8$ alkyl, or $R^5$ and $R^6$ together with the atoms to which they are linked join to form a 5 to 6-membered heterocyclic ring; and
- wherein n is an integer from 1 to 6; and m is an integer from 0 to 2;
- wherein each of the above alkyl, aryl, heteroaryl, cycloalkyl, heterocyclyl moieties and heterocyclic rings are optionally and independently substituted by 1-3 substituents selected from
  - amino,
  - aryl, heteroaryl, cycloalkyl, or heterocyclyl optionally substituted by 1-5 substituents selected from
    - $C_1$-$C_6$ alkoxy,
    - $C_1$-$C_6$ alkyl optionally substituted by halo,
    - aryl,
    - halo,
    - heteroaryl,
    - $C_1$-$C_6$ hydroxyl, and
    - —NHS(O)$_2$—($C_1$-$C_6$ alkyl);
  - $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamino, $C_2$-$C_6$ alkenyl, or $C_2$-$C_6$ alkynyl, wherein each of which may be interrupted by one or more hetero atoms,
  - cyano,
  - halo,
  - hydroxy,
  - nitro, or
  - —O-aryl;

or a pharmaceutically acceptable salt, or stereoisomer thereof.

2. The compound of claim 1 or pharmaceutically acceptable salt, or stereoisomer thereof, wherein m and n are 1.

3. The compound of claim 1 or pharmaceutically acceptable salt, or stereoisomer thereof, wherein $R^1$ is heteroaryl, $R^3$ is aryl or heteroaryl, and m and n are 1.

4. The compound of claim 3 or pharmaceutically acceptable salt, or stereoisomer thereof, wherein $R^5$ and $R^6$ are —H.

5. The compound of claim 1 wherein the compound is N²-[5-(3-methyl-1H-indazol-5-yl)-[1,3,4]thiadiazol-2-yl]-1-(1,2,3,4-tetrahydro-naphthalen-2-yl)-ethane-1,2-diamine.

6. The compound of claim 1, wherein the compound is N—((S)-2-amino-2-(2,3-dihydro-1H-inden-2-yl)ethyl)-5-(3-methyl-1H-indazol-5-yl)-1,3,4-thiadiazol-2-amine.

7. The compound of claim 1, wherein the compound is N—((S)-2-amino-2-(2,3-dihydro-1H-inden-2-yl)ethyl)-5-(1H-indazol-5-yl)-1,3,4-thiadiazol-2-amine.

8. The compound of claim 1, wherein the compound is N—((S)-2-amino-2-((R)-2,3-dihydro-1H-inden-1-yl)ethyl)-5-(3-methyl-1H-indazol-5-yl)-1,3,4-thiadiazol-2-amine.

9. A pharmaceutical composition comprising a pharmaceutically-acceptable carrier and a compound of claim 1.

* * * * *